(12) United States Patent
Weber

(10) Patent No.: US 11,883,283 B2
(45) Date of Patent: Jan. 30, 2024

(54) TRANSCATHETER ATRIO-VENTRICULAR VALVE PROSTHESIS

(71) Applicant: HIGHLIFE SAS, Paris (FR)

(72) Inventor: Josef Weber, Neufahrn (DE)

(73) Assignee: HIGHLIFE SAS, Paris (FR)

( * ) Notice: Subject to any disclaimer, the term of this patent is extended or adjusted under 35 U.S.C. 154(b) by 0 days.

(21) Appl. No.: 17/884,100

(22) Filed: Aug. 9, 2022

(65) Prior Publication Data
US 2022/0378573 A1 Dec. 1, 2022

Related U.S. Application Data

(60) Continuation of application No. 16/685,062, filed on Nov. 15, 2019, now Pat. No. 11,446,140, which is a (Continued)

(30) Foreign Application Priority Data

Aug. 3, 2010 (DE) .......................... 102010036824.5

(51) Int. Cl.
*A61F 2/24* (2006.01)
*A61B 17/064* (2006.01)
(Continued)

(52) U.S. Cl.
CPC .......... *A61F 2/2418* (2013.01); *A61F 2/2409* (2013.01); *A61F 2/2442* (2013.01); (Continued)

(58) Field of Classification Search
CPC .... A61F 2/2418; A61F 2/2409; A61F 2/2427; A61F 2/2475
See application file for complete search history.

(56) References Cited

U.S. PATENT DOCUMENTS 3,409,013 A 11/1968 Berry
3,548,417 A 12/1970 Kischer
(Continued)

FOREIGN PATENT DOCUMENTS

AU 2006203499 A1 8/2006
CA 2414022 A1 1/2002
(Continued)

OTHER PUBLICATIONS

D.N. Ross, "Aortic Valve Surgery," The Annals of the Royal College of Surgeons of England, Sep. 1966, pp. 192-197.
(Continued)

*Primary Examiner* — Suba Ganesan
(74) *Attorney, Agent, or Firm* — Oliff PLC

(57) ABSTRACT

A transcatheter atrio-ventricular valve prosthesis for functional replacement of an atrio-ventricular valve in a connection channel, having a circumferential connection channel wall structure, between atrial and ventricular chambers of a heart, including an inner device to be disposed in the interior of the connection channel, the inner device having a circumferential support structure which is radially expandable and having a valve attached to the circumferential support structure, and an outer device to be disposed on the exterior of the connection channel, wherein the outer device at least partly extends around the inner device at a radial distance to the inner device, wherein the inner and outer devices form a securing mechanism for securing the circumferential connection channel wall structure therebetween.

19 Claims, 31 Drawing Sheets

Related U.S. Application Data continuation of application No. 15/884,953, filed on Jan. 31, 2018, now Pat. No. 11,259,921, which is a continuation of application No. 15/153,333, filed on May 12, 2016, now Pat. No. 9,931,206, which is a division of application No. 13/808,838, filed as application No. PCT/IB2011/002282 on Jun. 30, 2011, now Pat. No. 9,375,312.

(60) Provisional application No. 61/363,070, filed on Jul. 9, 2010.

(51) Int. Cl.
  *A61B 17/122* (2006.01)
  *A61B 17/128* (2006.01)
  *A61B 17/00* (2006.01)
  *A61B 17/04* (2006.01)

(52) U.S. Cl.
  CPC ......... *A61B 17/064* (2013.01); *A61B 17/1227* (2013.01); *A61B 17/1285* (2013.01); *A61B 2017/003* (2013.01); *A61B 2017/0403* (2013.01); *A61B 2017/0427* (2013.01); *A61B 2017/0464* (2013.01); *A61B 2017/0475* (2013.01); *A61F 2/2427* (2013.01); *A61F 2/2457* (2013.01); *A61F 2/2475* (2013.01); *A61F 2210/0057* (2013.01); *A61F 2220/005* (2013.01); *A61F 2220/0008* (2013.01); *A61F 2220/0016* (2013.01); *A61F 2220/0066* (2013.01); *A61F 2230/0067* (2013.01); *A61F 2230/0091* (2013.01); *A61F 2250/001* (2013.01); *A61F 2250/006* (2013.01); *A61F 2250/007* (2013.01); *A61F 2250/0063* (2013.01); *A61F 2250/0069* (2013.01)

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Azarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Eckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,383,905 A | 1/1995 | Golds et al. |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Eone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Eonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Touser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,735 B1 | 1/2002 | Stevens |
| 6,350,277 B1 | 2/2002 | Kocur |
| 6,419,696 B1 | 7/2002 | Ortiz et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |

(56) References Cited

U.S. PATENT DOCUMENTS

| | | |
|---|---|---|
| 6,488,704 B1 | 12/2002 | Connelly et al. |
| 6,537,314 B2 | 3/2003 | Langberg et al. |
| 6,540,782 B1 | 4/2003 | Snyders |
| 6,569,196 B1 | 5/2003 | Vesely |
| 6,582,462 B1 | 6/2003 | Andersen et al. |
| 6,605,112 B1 | 8/2003 | Moll et al. |
| 6,629,534 B1 | 10/2003 | St. Goar et al. |
| 6,730,118 B2 | 5/2004 | Spenser et al. |
| 6,733,525 B2 | 5/2004 | Yang et al. |
| 6,752,813 B2 | 6/2004 | Goldfarb et al. |
| 6,830,584 B1 | 12/2004 | Seguin |
| 6,875,231 B2 | 4/2005 | Anduiza et al. |
| 6,893,460 B2 | 5/2005 | Spenser et al. |
| 6,908,481 B2 | 6/2005 | Cribier |
| 6,951,571 B1 | 10/2005 | Srivastava |
| 6,978,176 B2 | 12/2005 | Attouf |
| 7,018,406 B2 | 3/2006 | Seguin et al. |
| 7,025,780 B2 | 4/2006 | Gabbay |
| 7,033,390 B2 | 4/2006 | Johnson et al. |
| 7,041,132 B2 | 5/2006 | Quijano et al. |
| 7,101,396 B2 | 9/2006 | Artof et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,320,704 B2 | 1/2008 | Lashinski et al. |
| 7,329,279 B2 | 2/2008 | Haug et al. |
| 7,364,588 B2 | 4/2008 | Mathis et al. |
| 7,374,571 B2 | 5/2008 | Pease et al. |
| 7,381,219 B2 | 6/2008 | Salahieh et al. |
| 7,393,360 B2 | 7/2008 | Spenser et al. |
| 7,399,315 B2 | 7/2008 | Iobbi |
| 7,429,269 B2 | 9/2008 | Schwammenthal et al. |
| 7,442,204 B2 | 10/2008 | Schwammenthal et al. |
| 7,445,630 B2 | 11/2008 | Lashinski et al. |
| 7,462,191 B2 | 12/2008 | Spenser et al. |
| 7,534,259 B2 | 5/2009 | Lashinski et al. |
| 7,588,582 B2 | 9/2009 | Starksen et al. |
| 7,618,446 B2 | 11/2009 | Andersen et al. |
| 7,621,948 B2 | 11/2009 | Herrmann et al. |
| 7,641,686 B2 | 1/2010 | Lashinski et al. |
| 7,641,688 B2 | 1/2010 | Lesh |
| 7,666,193 B2 | 2/2010 | Starksen et al. |
| 7,717,955 B2 | 5/2010 | Lane et al. |
| 7,722,666 B2 | 5/2010 | Lafontaine |
| 7,744,912 B1 | 6/2010 | Hubbell et al. |
| 7,753,949 B2 | 7/2010 | Amphere et al. |
| 7,803,185 B2 | 9/2010 | Gabbay |
| 8,070,802 B2 | 12/2011 | Amphere et al. |
| 8,092,520 B2 | 1/2012 | Quadri |
| 8,236,049 B2 | 8/2012 | Rowe et al. |
| 2001/0021872 A1 | 9/2001 | Bailey et al. |
| 2002/0032481 A1 | 3/2002 | Gabbay |
| 2002/0138135 A1 | 9/2002 | Duerig et al. |
| 2002/0143393 A1 | 10/2002 | Cox |
| 2002/0151970 A1 | 10/2002 | Garrison et al. |
| 2002/0173842 A1 | 11/2002 | Buchanan |
| 2003/0004079 A1 | 1/2003 | Aigner et al. |
| 2003/0014104 A1 | 1/2003 | Cribier |
| 2003/0036791 A1 | 2/2003 | Philipp et al. |
| 2003/0040792 A1 | 2/2003 | Gabbay |
| 2003/0050694 A1 | 3/2003 | Yang et al. |
| 2003/0069635 A1 | 4/2003 | Cartledge et al. |
| 2003/0100939 A1 | 5/2003 | Yodfat et al. |
| 2003/0114913 A1 | 6/2003 | Spenser et al. |
| 2003/0149476 A1 | 8/2003 | Damm et al. |
| 2003/0163194 A1 | 8/2003 | Quijano et al. |
| 2003/0198722 A1 | 10/2003 | Johnston et al. |
| 2003/0212454 A1 | 11/2003 | Scott et al. |
| 2003/0220245 A1 | 11/2003 | Hubbell et al. |
| 2003/0233142 A1 | 12/2003 | Morales et al. |
| 2004/0039436 A1 | 2/2004 | Spenser et al. |
| 2004/0049266 A1 | 3/2004 | Anduiza et al. |
| 2004/0092858 A1 | 5/2004 | Wilson et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0138745 A1 | 7/2004 | Macoviak et al. |
| 2004/0186563 A1 | 9/2004 | Lobbi |
| 2004/0186565 A1 | 9/2004 | Schreck |
| 2004/0225355 A1 | 11/2004 | Stevens |
| 2004/0236418 A1 | 11/2004 | Stevens |
| 2004/0243230 A1 | 12/2004 | Navia et al. |
| 2004/0260389 A1 | 12/2004 | Case et al. |
| 2004/0260393 A1 | 12/2004 | Rahdert et al. |
| 2005/0033398 A1 | 2/2005 | Seguin |
| 2005/0055089 A1 | 3/2005 | Macoviak et al. |
| 2005/0137688 A1 | 6/2005 | Salahieh et al. |
| 2005/0137691 A1 | 6/2005 | Salahieh et al. |
| 2005/0197696 A1 | 9/2005 | Gomez Duran |
| 2005/0234546 A1 | 10/2005 | Nugent et al. |
| 2006/0025854 A1 | 2/2006 | Lashinski et al. |
| 2006/0025857 A1 | 2/2006 | Bergheim et al. |
| 2006/0089671 A1 | 4/2006 | Goldfarb et al. |
| 2006/0149350 A1 | 7/2006 | Patel et al. |
| 2006/0195134 A1 | 8/2006 | Crittenden |
| 2006/0229719 A1 | 10/2006 | Marquez et al. |
| 2006/0259135 A1 | 11/2006 | Navia et al. |
| 2006/0259137 A1 | 11/2006 | Artof et al. |
| 2006/0271166 A1 | 11/2006 | Thill et al. |
| 2007/0005129 A1 | 1/2007 | Damm et al. |
| 2007/0005131 A1 | 1/2007 | Taylor |
| 2007/0005133 A1 | 1/2007 | Lashinski et al. |
| 2007/0016286 A1 | 1/2007 | Herrmann et al. |
| 2007/0016288 A1 | 1/2007 | Gurskis et al. |
| 2007/0100439 A1 | 5/2007 | Cangialosi et al. |
| 2007/0112422 A1 | 5/2007 | Dehdashtian |
| 2007/0142906 A1 | 6/2007 | Figulla et al. |
| 2007/0162107 A1 | 7/2007 | Haug et al. |
| 2007/0168024 A1 | 7/2007 | Khairkhahan |
| 2007/0213813 A1 | 9/2007 | Von Segesser et al. |
| 2007/0255396 A1 | 11/2007 | Douk et al. |
| 2007/0270944 A1 | 11/2007 | Bergheim et al. |
| 2008/0004697 A1 | 1/2008 | Lichtenstein et al. |
| 2008/0033543 A1 | 2/2008 | Gurskis et al. |
| 2008/0039934 A1 | 2/2008 | Styrc |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077234 A1 | 3/2008 | Styrc |
| 2008/0091264 A1 | 4/2008 | Machold et al. |
| 2008/0147183 A1 | 6/2008 | Styrc |
| 2008/0154355 A1 | 6/2008 | Benichou et al. |
| 2008/0208328 A1 | 8/2008 | Antocci et al. |
| 2008/0208332 A1 | 8/2008 | Amphere et al. |
| 2008/0221672 A1 | 9/2008 | Amphere et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0269878 A1 | 10/2008 | Iobbi |
| 2009/0012356 A1 | 1/2009 | Dann et al. |
| 2009/0012602 A1 | 1/2009 | Quadri |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0149872 A1 | 6/2009 | Gross et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0216314 A1 | 8/2009 | Quadri |
| 2009/0222076 A1 | 9/2009 | Figulla et al. |
| 2009/0259307 A1 | 10/2009 | Gross et al. |
| 2009/0270858 A1 | 10/2009 | Hauck et al. |
| 2009/0276040 A1 | 11/2009 | Rowe et al. |
| 2009/0281609 A1 | 11/2009 | Benichou et al. |
| 2009/0287298 A1 | 11/2009 | Jenson et al. |
| 2009/0287299 A1 | 11/2009 | Tabor et al. |
| 2009/0319037 A1 | 12/2009 | Rowe et al. |
| 2010/0001001 A1 | 1/2010 | Seline |
| 2010/0004740 A1 | 1/2010 | Seguin et al. |

(56) References Cited

U.S. PATENT DOCUMENTS

| | | |
|---|---|---|
| 2010/0016958 A1 | 1/2010 | St. Goar et al. |
| 2010/0036479 A1 | 2/2010 | Hill et al. |
| 2010/0036484 A1 | 2/2010 | Hariton et al. |
| 2010/0036485 A1 | 2/2010 | Seguin |
| 2010/0042208 A1 | 2/2010 | Herrmann et al. |
| 2010/0049303 A1 | 2/2010 | Guyenot et al. |
| 2010/0049315 A1 | 2/2010 | Kirson |
| 2010/0069852 A1 | 3/2010 | Kelley |
| 2010/0070027 A1 | 3/2010 | Bonhoeffer et al. |
| 2010/0076548 A1 | 3/2010 | Konno |
| 2010/0082089 A1 | 4/2010 | Quadri et al. |
| 2010/0082094 A1 | 4/2010 | Quadri et al. |
| 2010/0082098 A1 | 4/2010 | Starksen et al. |
| 2010/0100176 A1 | 4/2010 | Elizondo et al. |
| 2010/0121435 A1 | 5/2010 | Subramanian et al. |
| 2010/0121437 A1 | 5/2010 | Subramanian et al. |
| 2010/0137397 A1 | 6/2010 | Birch et al. |
| 2010/0141047 A1 | 6/2010 | Gibbs et al. |
| 2010/0141847 A1 | 6/2010 | Jayaram et al. |
| 2010/0145438 A1 | 6/2010 | Barone |
| 2010/0161042 A1 | 6/2010 | Maisano et al. |
| 2010/0174363 A1 | 7/2010 | Castro |
| 2010/0198347 A1 | 8/2010 | Zakay et al. |
| 2010/0210899 A1 | 8/2010 | Schankereli |
| 2010/0217382 A1 | 8/2010 | Chau et al. |
| 2010/0249917 A1 | 9/2010 | Zhang |
| 2010/0249918 A1 | 9/2010 | Zhang |
| 2010/0256751 A1 | 10/2010 | Rowe et al. |
| 2010/0262232 A1 | 10/2010 | Annest |
| 2010/0280495 A1 | 11/2010 | Paul et al. |
| 2010/0280604 A1 | 11/2010 | Zipory et al. |
| 2010/0292785 A1 | 11/2010 | Seguin et al. |
| 2010/0298931 A1 | 11/2010 | Quadri et al. |
| 2010/0312333 A1 | 12/2010 | Navia et al. |
| 2010/0331971 A1 | 12/2010 | Keranen et al. |
| 2011/0004296 A1 | 1/2011 | Lutter et al. |
| 2011/0029072 A1 | 2/2011 | Gabbay |
| 2011/0060407 A1 | 3/2011 | Ketai et al. |
| 2011/0071625 A1 | 3/2011 | Hill et al. |
| 2011/0106244 A1 | 5/2011 | Ferrari et al. |
| 2011/0111047 A1 | 5/2011 | Young |
| 2011/0112632 A1 | 5/2011 | Chau et al. |
| 2011/0125258 A1 | 5/2011 | Centola |
| 2011/0137397 A1* | 6/2011 | Chau .................. A61F 2/2412 623/2.37 |
| 2011/0178597 A9 | 7/2011 | Navia et al. |
| 2011/0184510 A1 | 7/2011 | Maisano et al. |
| 2011/0208297 A1 | 8/2011 | Tuval et al. |
| 2011/0208298 A1 | 8/2011 | Tuval et al. |
| 2011/0213460 A1 | 9/2011 | Lashinski et al. |
| 2011/0224785 A1 | 9/2011 | Hacohen |
| 2011/0251684 A1 | 10/2011 | Rahdert et al. |
| 2011/0264196 A1 | 10/2011 | Savage et al. |
| 2011/0295059 A1 | 12/2011 | Machold et al. |
| 2011/0313515 A1 | 12/2011 | Quadri et al. |
| 2011/0319988 A1 | 12/2011 | Schankereli et al. |
| 2012/0010700 A1 | 1/2012 | Spenser |
| 2012/0016464 A1 | 1/2012 | Seguin |
| 2012/0022639 A1 | 1/2012 | Hacohen et al. |
| 2012/0022640 A1 | 1/2012 | Gross et al. |
| 2012/0101572 A1 | 4/2012 | Kovalsky et al. |
| 2012/0179244 A1 | 7/2012 | Schankereli et al. |
| 2012/0191182 A1 | 7/2012 | Hauser et al. |
| 2012/0197388 A1 | 8/2012 | Khairkhahan et al. |
| 2012/0203336 A1 | 8/2012 | Annest |
| 2012/0209376 A1 | 8/2012 | Hauser et al. |
| 2012/0209377 A1 | 8/2012 | Machold et al. |
| 2012/0226349 A1 | 9/2012 | Tuval et al. |
| 2012/0303116 A1 | 11/2012 | Gorman, III et al. |
| 2012/0323316 A1 | 12/2012 | Chau et al. |
| 2013/0096673 A1 | 4/2013 | Hill et al. |

FOREIGN PATENT DOCUMENTS

| | | |
|---|---|---|
| CN | 1714766 A | 1/2006 |
| DE | 195 32 846 A1 | 3/1997 |
| DE | 199 07 646 A1 | 8/2000 |
| DE | 195 46 692 C2 | 11/2002 |
| DE | 100 49 812 B4 | 6/2004 |
| DE | 198 57 887 B4 | 5/2005 |
| DE | 601 11 184 T2 | 10/2005 |
| DE | 10 2006 052 564 B3 | 12/2007 |
| DE | 10 2007 049 404 A1 | 5/2008 |
| DE | 692 33 715 T2 | 10/2008 |
| DE | 20 2008 009 610 U1 | 12/2008 |
| DE | 10 2007 043 830 A1 | 4/2009 |
| EP | 0 103 546 B1 | 5/1988 |
| EP | 0 144 167 B1 | 11/1989 |
| EP | 0 592 410 A1 | 4/1994 |
| EP | 0 597 967 A1 | 5/1994 |
| EP | 0 850 607 A1 | 7/1998 |
| EP | 1 057 460 A1 | 12/2000 |
| EP | 1 629 795 B1 | 6/2004 |
| EP | 1 469 797 A1 | 10/2004 |
| EP | 1 088 529 B1 | 6/2005 |
| EP | 1 702 247 A2 | 9/2006 |
| EP | 1 570 809 B1 | 1/2009 |
| EP | 205 5 266 A2 | 5/2009 |
| EP | 2 260 798 A2 | 12/2010 |
| NO | 2011/106533 A1 | 9/2011 |
| WO | 91/17720 A1 | 11/1991 |
| WO | 92/17118 A1 | 10/1992 |
| WO | 93/01768 A1 | 2/1993 |
| WO | 97/24080 A1 | 7/1997 |
| WO | 98/29057 A1 | 7/1998 |
| WO | 99/33414 A1 | 7/1999 |
| WO | 99/40964 A1 | 8/1999 |
| WO | 99/47075 A1 | 9/1999 |
| WO | 00/18333 A1 | 4/2000 |
| WO | 00/41652 A1 | 7/2000 |
| WO | 00/47139 A1 | 8/2000 |
| WO | 01/35878 A2 | 5/2001 |
| WO | 01/49213 A2 | 7/2001 |
| WO | 01/54624 A1 | 8/2001 |
| WO | 01/54625 A1 | 8/2001 |
| WO | 01/56512 A1 | 8/2001 |
| WO | 01/62189 A1 | 8/2001 |
| WO | 01/64137 A1 | 9/2001 |
| WO | 01/76510 A2 | 10/2001 |
| WO | 02/003892 A1 | 1/2002 |
| WO | 02/05731 A1 | 1/2002 |
| WO | 02/22054 A1 | 3/2002 |
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 03/003943 A2 | 1/2003 |
| WO | 03/047468 A1 | 6/2003 |
| WO | 03/080150 A2 | 10/2003 |
| WO | 2004/014282 A2 | 2/2004 |
| WO | 2004/026117 A2 | 4/2004 |
| WO | 2004/032724 A2 | 4/2004 |
| WO | 2004/112651 A2 | 12/2004 |
| WO | 2004/112657 A1 | 12/2004 |
| WO | 2005/062980 A2 | 7/2005 |
| WO | 2005/070343 A1 | 8/2005 |
| WO | 2005/072655 A1 | 8/2005 |
| WO | 2005/079706 A1 | 9/2005 |
| WO | 2005/087140 A1 | 9/2005 |
| WO | 2006/014233 A2 | 2/2006 |
| WO | 2006/034008 A2 | 3/2006 |
| WO | 2006/054930 A1 | 5/2006 |
| WO | 2006/113906 A1 | 10/2006 |
| WO | 2006/121450 A1 | 11/2006 |
| WO | 2006/127756 A2 | 11/2006 |
| WO | 2006/127765 A1 | 11/2006 |
| WO | 2006/128185 A2 | 11/2006 |
| WO | 2006/128193 A2 | 11/2006 |
| WO | 2007/009117 A1 | 1/2007 |
| WO | 2007/016187 A2 | 2/2007 |

(56) References Cited

FOREIGN PATENT DOCUMENTS

| | | |
|---|---|---|
| WO | 2007/025028 A1 | 3/2007 |
| WO | 2007/053243 A2 | 5/2007 |
| WO | 2007/075394 A2 | 7/2007 |
| WO | 2008/005405 A2 | 1/2008 |
| WO | 2008/013915 A2 | 1/2008 |
| WO | 2008/035337 A2 | 3/2008 |
| WO | 2008/070224 A2 | 6/2008 |
| WO | 2008/089365 A2 | 7/2008 |
| WO | 2008/091515 A2 | 7/2008 |
| WO | 2008/092101 A2 | 7/2008 |
| WO | 2008/095475 A2 | 8/2008 |
| WO | 2008/103497 A2 | 8/2008 |
| WO | 2008/103498 A2 | 8/2008 |
| WO | 2008/103722 A2 | 8/2008 |
| WO | 2008/106531 A1 | 9/2008 |
| WO | 2008/125153 A1 | 10/2008 |
| WO | 2008/147964 A1 | 12/2008 |
| WO | 2008/150529 A1 | 12/2008 |
| WO | 2009/014617 A1 | 1/2009 |
| WO | 2009/024859 A2 | 2/2009 |
| WO | 2009/026563 A2 | 2/2009 |
| WO | 2009/033469 A1 | 3/2009 |
| WO | 2009/052188 A1 | 4/2009 |
| WO | 2009/053497 A1 | 4/2009 |
| WO | 2009/085206 A2 | 7/2009 |
| WO | 2009/085207 A1 | 7/2009 |
| WO | 2009/092782 A1 | 7/2009 |
| WO | 2009/108355 A1 | 9/2009 |
| WO | 2009/132187 A1 | 10/2009 |
| WO | 2009/134701 A2 | 11/2009 |
| WO | 2009/140268 A1 | 11/2009 |
| WO | 2009/149215 A1 | 12/2009 |
| WO | 2009/155561 A2 | 12/2009 |
| WO | 2010/007609 A1 | 1/2010 |
| WO | 2010/033936 A2 | 3/2010 |
| WO | 2010/037141 A1 | 4/2010 |
| WO | 2010/042950 A2 | 4/2010 |
| WO | 2010/057262 A1 | 5/2010 |
| WO | 2010/080594 A2 | 7/2010 |
| WO | 2010/086460 A1 | 8/2010 |
| WO | 2010/090878 A2 | 8/2010 |
| WO | 2010/091653 A1 | 8/2010 |
| WO | 2010/093837 A2 | 8/2010 |
| WO | 2010/099032 A2 | 9/2010 |
| WO | 2010/117471 A2 | 10/2010 |
| WO | 2010/117589 A2 | 10/2010 |
| WO | 2010/117609 A2 | 10/2010 |
| WO | 2010/117680 A1 | 10/2010 |
| WO | 2010/121076 A2 | 10/2010 |
| WO | 2010/127041 A1 | 11/2010 |
| WO | 2010/141047 A1 | 12/2010 |
| WO | 2010/141847 A1 | 12/2010 |
| WO | 2011/051043 A1 | 5/2011 |
| WO | 2011/072084 A2 | 6/2011 |
| WO | 2011/106137 A1 | 9/2011 |
| WO | 2011/106544 A1 | 9/2011 |
| WO | 2011/109813 A2 | 9/2011 |
| WO | 2011/111047 A2 | 9/2011 |
| WO | 2011/137531 A1 | 11/2011 |
| WO | 2012/063228 A1 | 5/2012 |

OTHER PUBLICATIONS

Poncin et al., Nitinol Tubular Stents: Comparing Two Manufacturing Methods, Proceedings of the First European Conference on Shape Memory and Superelastic Technologies, 1999, pp. 165-170.
Boudjemline et al, "Steps Toward Percutaneous Aortic Valve Replacement", Journal of the American Heart Association, Feb. 12, 2002.
"Direct Flow Medical Announces Fifth Patent Issuance of Their Unique Percutaneous Aortic Valve Technology", Santa Rosa, California, May 19, 2009.
Andersen, et al, "Transluminal implantation of articifial heart valves, Description of a new expandable aortic valve and initial results with implantation by catheter technique in closed chest pigs", Eur Heart J., May 1992, vol. 103, No. 5, pp. 704-708 (Abstract). (retrieved from http://ncbi.nlm.nih.gov/pubmed?term=1618213%5Buid%5D).
Inoue et al., "Clinical application of transvenous mitral commissurotomy by a new balloon catheter," J Thorac Cardiovasc Surg., Mar. 1984, vol. 87, No. 3, pp. 394-402. (Abstract). (retrieved from http://www.ncbi.nlm.nih.gov/pubmed?term=6700245%5Buid%5D).
Lawrence, Jr. et al., "Percutaneous endvascular graft: experimental evaluation," Radiology, May 1987, vol. 163, No. 2, pp. 357-3690. (Abstract). (retrieved from http://www.Ncbi.nlm.nih.gov/pubmed?term=2951767%5Buid%5D).
Pavcnik et al., "Development and initial experimental evaluation of a prosthetic aortic valve for transcatheter placement. Work in progress," Radiology, Apr. 1992, vol. 183, No. 1, pp. 151-154. (Abstract) (retrieved from http://www.Ncbi.nlm.nih.gov/pubmed?term=1549662).
Sabbah et al., "Mechanical factors in the degeneration of porcine bioprosthetic valves: an overview", J Card Surg, Dec. 1989, vol. 4, No. 4, pp. 302-309 (Abstract). (retrieved from http://www.ncbi.nlm.nih.gov/pubmed?term=252009%5Buid%5D).
Selby et al., "Experience with new retrieval forceps for foreign body removal in the vascular, urinary, and billiary systems", Radiology, Aug. 1990, vol. 176, No. 2, pp. 535-538. (Abstract). (retrieved from http://www.ncbi.nlm.nih.gov/pubmed?term=2367671%5Buid%5D).
Al Zaibag et al., "Percutaneous balloon valvotomy in tricuspid stenosis," Br Heart J, Case Reports, 1987, vol. 57, pp. 51-53. (retrieved froom http://www.heartbmj.com).
Al-Khaja et al., "Eleven years' experience with Carpentier-Edwards biological valves in relation to survival and complications," European Journal of Cardio-Thoracic Surgery, 1989, vol. 3, pp. 305-311.
Almagor et al., "Balloon Expandable Stent Implantation in Stenotic Right Hear Valved Conduits," JACC, Nov. 1, 1990, vol. 16, No. 5, pp. 1310-1314.
Benchimol et al., "Simultaneous left ventricular echocardiography and aortic blood velocity during rapid right ventricular pacing in man," The American Journal of the Medical Sciences, Jan.-Feb. 1977, vol. 273, No. 1, pp. 55-62.
Dotter et al., "Transluminal Treatment of Arteriosclerotic Obstruction", Curculation, vol. XXX, Nov. 1964, pp. 654-670.
Kolata, "Device That Opens Clogged Arteries Gets a Failing Grade in a New Study," Jan. 3, 1991 (retrieved from http://www.nytimes.com/articles.html).
Rashkind et al., "Creation of an Atrial Septal Defect Without Thoracotomy," JAMA, Jun. 13, 1966, vol. 196, No. 11, pp. 173-174.
Rashkind et al., "Historical Aspects of Interventional Cardiology: Past, Present and Future," Texas Heart Institute Journal, vol. 13, No. 4, Dec. 1986, pp. 363-367.
Rosch et al., "The Birth, Early Years, and Future of Interventional Radiology," Radiol, 2003, vol. 14, pp. 841-853.
Uchida et al., "Modifications of Gianturco Expandable Wire Stents," AJR, May 1988, vol. 150, pp. 1185-1187.
Watt et al., "Intravenous adenosine in the treatment of supraventricular tachycardia: a dose-ranging study and Interactions with dipyridamole," Br. J. cln. Pharmac, 1986, vol. 21, pp. 227-230.
Antona, et al., "Hybrid Technique for Total Arch Repair: Aortic Neck Reshaping for Endovascular-Graft Fixation," The Annals of Thoracic Surgery, 2007, vol. 83, pp. 1158-1161.
Jun. 1, 2017 Office Action issued in U.S. Appl. No. 15/153,333.
Walher et al. Transapical Minimally Invasive Aortic Valve Implantation; Multicenter Experience. Circulation 116,11 suppl. (2007).
Jan. 7, 2020 Office Action issued in U.S. Appl. No. 15/884,953.
Jun. 26, 2020 Office Action issued in U.S. Appl. No. 15/884,953.
Oct. 16, 2020 U.S. Office Action issued U.S. Appl. No. 15/884,953.
Apr. 9, 2021 Office Action issued in U.S. Appl. No. 15/884,953.
Jul. 20, 2021 Office Action issued in U.S. Appl. No. 16/685,018.
Oct. 21, 2021 Notice of Allowance issued in U.S. Appl. No. 16/684,751.

* cited by examiner

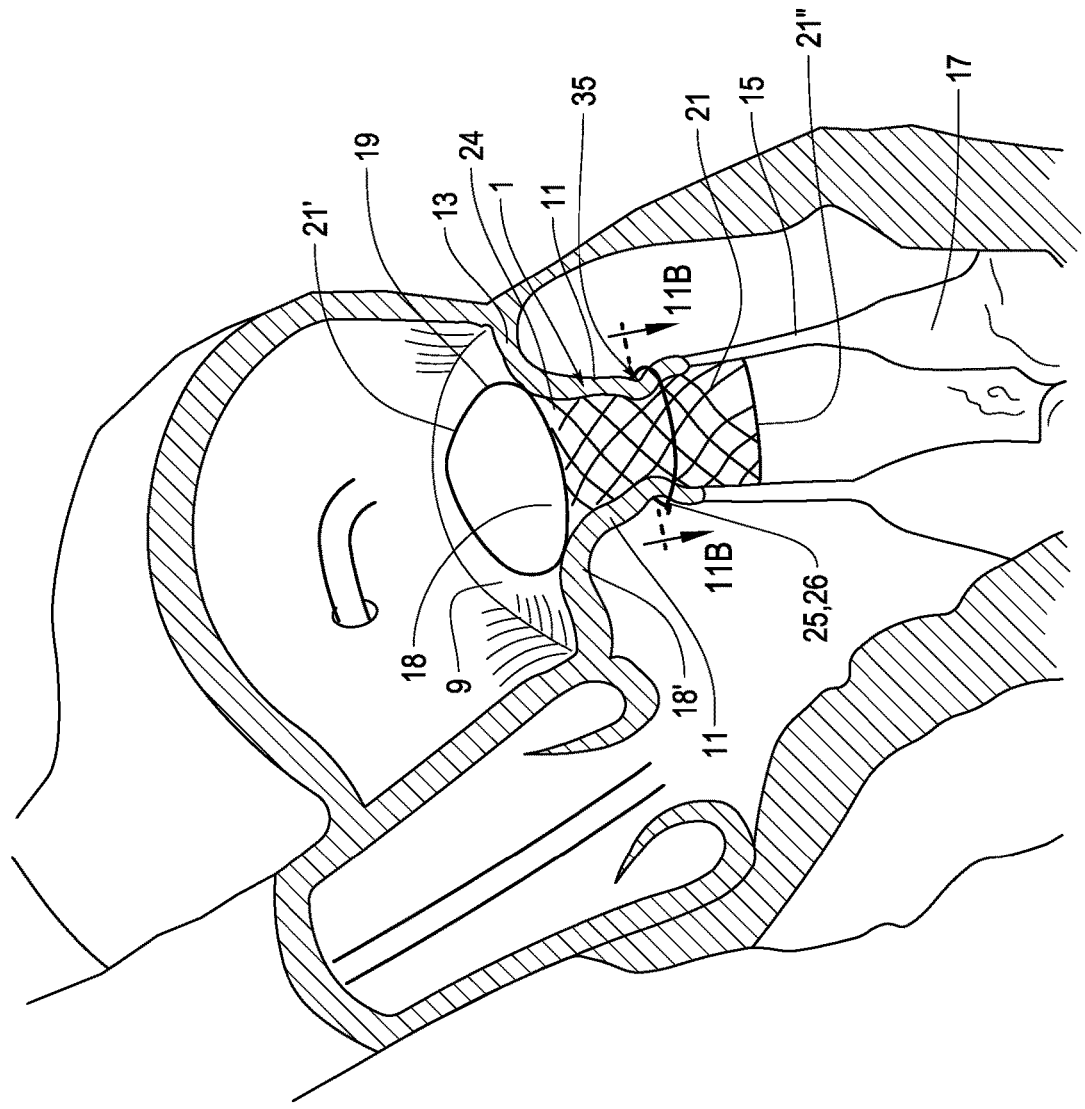
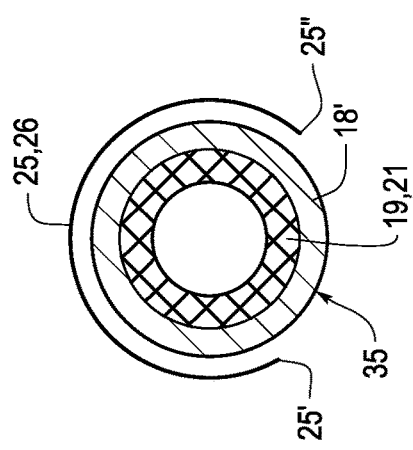
FIG. 11A
FIG. 11B

TRANSCATHETER ATRIO-VENTRICULAR VALVE PROSTHESIS

This application is a continuation application of U.S. patent application Ser. No. 16/685,062, filed Nov. 15, 2019, which in turn is a continuation application of U.S. patent application Ser. No. 15/884,953, filed Jan. 31, 2018, which in turn is a continuation application of U.S. patent application Ser. No. 15/153,333, filed May 12, 2016, which in turn is a divisional application of U.S. patent application Ser. No. 13/808,838, filed Jan. 7, 2013, which is a National Stage of PCT/IB2011/002282, filed Jun. 30, 2011. The present application claims priority and benefit of U.S. provisional application No. 61/363,070 and of German patent application No. 10 2010 036 824.5. The entire content of the prior applications is incorporated herein by reference.

FIELD OF INVENTION

The invention relates to atrio-ventricular valve (mitral valve or tricuspid valve) replacement devices for functionally replacing the corresponding native atrio-ventricular valve, and, in more detail, to a transcatheter atrio-ventricular valve replacement device or transcatheter atrio-ventricular valve prosthesis which allows implantation by means of a percutaneous approach, that is, a minimally invasive approach on a beating heart.

MEDICAL BACKGROUND

Normally the mitral valve allows blood to flow freely from the left atrial chamber to the left ventricular chamber during diastole when the heart is relaxed and prevents the backflow of blood from the left ventricle to the left atrium during systole when the heart contracts. The mitral valve or mitral valve structure has a generally circumferential wall structure forming a connection channel or through opening between the atrial and ventricular chambers of the heart and including a circumferential valve annulus, valve leaflets opening and closing the connection channel/through opening at a position close to the valve annulus, a generally circumferential chord structure (chordae tendinae) connected between the valve leaflets and generally circumferential papillary muscle(s), and said circumferential papillary muscle(s).

Proper opening and closing of the mitral valve leaflets depends on the coordinated function of its individual components i.e., the mitral annulus, the anterior and posterior mitral valve leaflets, chordae tendineae, papillary muscles, and the left atrial and left ventricular (LV) walls in continuity with the leaflets, and papillary muscles, respectively.

Mitral valve disease can take the form of mitral stenosis or mitral regurgitation. Mitral stenosis results when the valve does not open fully during diastole. In this case, higher than normal pressures are required to push blood forward into the left ventricle. Mitral regurgitation (MR) is a condition whereby the mitral valve does not close properly when the left ventricle contracts during left ventricular contraction. As a result, there is abnormal leaking of blood from the left ventricle into the left atrium.

Mitral pathology may basically be treated by valve repair or valve replacement. The treatment of mitral steno sis was revolutionized in 1984 and 1985 when Inoue and Lock developed percutaneous mitral balloon valvotomy. Echocardiography is essential for patient screening and predicting the likelihood of a successful percutaneous balloon mitral valvotomy (PBMV). Nevertheless, predicting the outcome of percutaneous mitral balloon valvotomy remains somewhat limited. In cases where the mitral valve leaflets are severely restricted, thickened, and/or calcified and the submitral apparatus is severely thickened and/or calcified, surgical mitral valve replacement or repair needs to be considered. Mitral valve surgery is also indicated in patients with concomitant moderate to severe mitral regurgitation or left atrial thrombus. Although there is some data comparing the outcomes of PBMV to surgical commissurotomy for patients with mitral stenosis, there is a paucity of data comparing the outcomes of PBMV to surgical mitral valve replacement. The outcomes of PBMV were just as good or better than surgical commissurotomy in patients who were candidates for PBMV.

Mitral regurgitation can result from an abnormality of the mitral valve leaflets or chordae tendinae, in which case it is called primary or degenerative mitral valve disease. On the other hand, mitral regurgitation can occur in the setting of normal mitral valve leaflets and chordae tendinae; known as secondary or functional mitral regurgitation. In this case, a dilated left ventricle from ischemic or non-ischemic origin can result in mitral annular dilatation or a change in position of the papillary muscles and lead to abnormal closing of the mitral valve leaflets.

Mitral regurgitation is an important health problem. It affects approximately 9% of the population above 75 years old. Of the 5 million patients suffering from heart failure in the United States, 15-20% are found to have moderate to severe mitral regurgitation. The occurrence of mitral regurgitation early after a myocardial infarction (MI) is reported to be 50% (mild in 38%, moderate-severe in 12%). Short- and long-term survival is worse when mitral regurgitation of any severity accompanies heart failure or a myocardial infarction.

Although surgical mitral valve repair or replacement remains the standard of care for patients with significant mitral valve disease, the European Heart Survey demonstrated that up to one-half of patients with severe symptomatic mitral regurgitation do not undergo surgery. Compared with those who underwent surgery, these patients were typically older, had impairment of left ventricular function, and had more noncardiac diseases than did patients undergoing valve surgery. Whether denying surgery in these patients was justified or not, the challenges of managing these patients will only increase in the coming years as the number of patients considered for surgery continues to rise.

Although surgical mitral valve repair and replacement can be associated with an acceptable mortality risk approaching 1% and 6%, respectively, it requires a sternotomy and cardiopulmonary bypass that can be associated with significant complications. More specifically, the occurrence of any major complication (e.g. operative mortality, myocardial infarction, tamponade, septicemia, stroke, re-operation, renal failure, deep wound infection, ventilatory support >24 hours and GI bleed) can be as high as 12% and 25% for mitral valve repair and replacement, respectively (STS database 2002).

Previous data published from the mid 1990's suggested that surgical mitral valve repair had better short- and long-term survival chances than mitral valve replacement (Circulation 1995; 91:1022). It is important to note that the Starr Edwards valve was the most frequently utilized mechanical valve in that study. Since then, there has been a better understanding of the techniques for surgical mitral valve replacement. For instance, preservation of the chords and maintaining the submitral apparatus intact during mitral valve replacement has been associated with improved indices of left ventricular end systolic function (Circulation 1992; 86:1718-1726). In addition, the use of bioprosthetic over mechanical mitral valves has been shown to reduce the incidence of valve-related complications such as bleeding (JACC 200; 36:1152-1158). In a propensity-matched analysis, the probability of re-operation was higher after mitral valve repair than mitral valve replacement.

Mitral valve annuloplasty is the cornerstone of mitral valve repair. Annuloplasty may be used together with leaflet repair (resection, sliding annuloplasty) or chordal reconstruction (transposition, artificial chords). For repair of a degenerative mitral valve, failure to include an annuloplasty procedure negatively affects the long-term results of the procedure.

The Alfieri procedure involves suturing the free edges of the middle anterior and middle posterior leaflets of the mitral valve. This produces a double orifice mitral valve. The procedure can be used to treat degenerative or functional mitral regurgitation Like leaflet repair, the Alfieri procedure requires concomitant annuloplasty to avoid repair failure.

The clinical benefits and durability of mitral valve repair in the setting of severe functional mitral regurgitation are controversial; especially in the setting of severe left ventricular dilatation and dysfunction (JACC 2008; 52:319-26) (JACC 2005; 45:381-7) (Circulation 1998; 98:Suppl II:124-7) (Sem Cardiovasc Surg 2002; 14:133-6). Furthermore, the respective role of mitral valve repair and replacement in this setting is also unclear. Although mitral valve replacement with chordal preservation is associated with a higher operative mortality than mitral valve repair, replacement offers a significantly lower failure rate. The failure rate of mitral valve repair for secondary mitral regurgitation can be as high as 30% at 1-2 years follow-up. Most of the literature pertaining to secondary mitral regurgitation and surgical therapy is based on mitral valve repair rather than mitral valve replacement. It can be hypothesized that the lack of mortality benefit associated with mitral valve repair is in some ways related to the poor durability results with mitral valve repair than mitral valve replacement.

In an effort to address the challenges ahead, researchers have been developing new options for a rapidly growing pool of patients in whom heart valve replacement or repair may be beneficial, but for whom surgical intervention is considered too high risk.

The goal of transcatheter valve therapy is to provide a treatment modality that is less invasive, associated with equal or greater efficacy compared with standard surgery, and is potentially safer compared to more invasive procedures.

To overcome limitations of surgical mitral valve implantation, several techniques have been proposed for minimally invasive or endovascular valve implantation in the mitral and/or tricuspid position.

Most catheter delivered devices are based on stents to enable collapsation and re-expansion, anchoring and sealing contact with the anatomy. Stents, whether balloon- or self-expandable, anchor by inner radial force on the anatomy. However the atrio-ventricular heart valves do not offer a substantially cylindrical location like a vessel or an aortic or pulmonary valve. Consequently anchoring by inner radial force is unstable. Furthermore, the valve annulus usually is very supple and extends significantly under inner radial force which can be deleterious to the anchoring and to the heart function. In addition the size and shape of the mitral valve annulus varies considerably in diseased valves. Therefore many different diameters for prosthetic replacement devices would be necessary.

Several authors have described alternative ways to anchor a valve prosthesis in the atrio-ventricular position. Some rely on a specific shape enabling a firm anchoring without the need of inner radial force like Hill et al. (US20100036479) describing a cage like construction filling the atrium and enabling to rest on the atrial wall over its complete surface. However, this technique will considerably impair atrial function, because atrial contraction is impeded. Quadri et al. (US2009306768) and Lamphere et al. (US20080221672) suggested the use of hooks engaging the valve annulus. Rowe et al. (US20090276040) described both a specific shape and a tether that can be anchored in the ventricular wall to resist dislodgment. Likewise Lutter (DE102007043830 A1) et al. describe a prosthesis which is anchored by broad extensions in the left atrium and held in place by countertraction through fixation in the left ventricular apex. In contrast Thambar et al. (US20080243245) describe a prosthesis which is anchored on the ventricular side of the mitral valve and held in place by countertraction through the left atrial wall. Both Palmaz et al. (WO03003943) and Leonhardt et al. (U.S. Pat. No. 5,957,949) suggest a prosthesis which is fixed in the mitral valve annulus by radial force, supported by some longitudinal compression through atrial and ventricular extensions. A different approach is presented by Laske et al. (WO 2008091515) who describe a two double barrel stent design, fixed in the mitral annulus by radial force.

While those authors describe means to achieve anchoring of a collapsible valve device, there is no clear description on how they achieve sealing contact to avoid peri-prosthetic leakages. Furthermore there is no mention on how the prosthesis can accommodate different ring sizes and shapes.

Furthermore, to avoid pushing the anterior mitral leaflet in the outflow tract and obstructing the blood flow out of the ventricle, such authors describe specific requirements. Quadri's device is anchored on the annulus and it does not reach inside the ventricle between the mitral leaflets but rather protrudes proximally inside the left atrium creating a no-flow zone and the risk of thrombus. Part of the free floating anterior leaflet which is not fixed by the hooks on the ventricular side of the stent may even protrude into the left ventricular outflow tract causing SAM. Rowe's device requires a distal end smaller than the proximal end.

All of the devices described above share the same potentially unresolved issues.
1. The mitral valve ring may give way to inner radial forces.
2. The variations in ring shape and size may not be fitted for all prostheses.
3. There could be mitral paravalvular regurgitation because the zone between the valve stent and the leaflet may not be sealed.
4. An anchoring through the apex restricts the prosthesis to the use by surgeons and may compress the left ventricle in its cranial-caudal dimension.

SUMMARY OF THE INVENTION

Embodiments of a transcatheter atrio-ventricular valve prosthesis for functional replacement of an atrio-ventricular valve in a connection channel, having a circumferential connection channel wall structure, between atrial and ventricular chambers of a heart, comprise an inner device to be disposed in the interior of the connection channel, the inner device having a circumferential support structure which is radially expandable and having a valve attached to the circumferential support structure, and an outer device to be disposed on the exterior of the connection channel, wherein the outer device at least partly extends around the inner device in a radial distance to the inner device, wherein the inner and outer devices form a clamping mechanism for clamping the circumferential connection channel wall structure therebetween. Further embodiments of the invention provide methods for implanting a transcatheter atrio-ventricular valve prosthesis.

Exemplary techniques and apparatuses, including prostheses, for practicing embodiments of the invention are shown in the attached figures and the descriptive appearing thereon. The features described herein can be used in various combinations, which are intended to be encompassed hereby. The disclosure of the embodiments as disclosed herein is not intended to restrict the invention to those specific embodiments, but to encompass all embodiments of the concepts addressed herein.

BRIEF DESCRIPTION OF THE DRAWINGS

FIG. 11A shows a schematic perspective view of a transcatheter atrio-ventricular valve prosthesis according to another embodiment of the invention.

FIG. 11B shows a section along line B-B in FIG. 11A.

In the figures, the same reference signs are used to identify same and similar parts and elements.

DESCRIPTION OF EMBODIMENTS OF THE INVENTION

Figure 1:
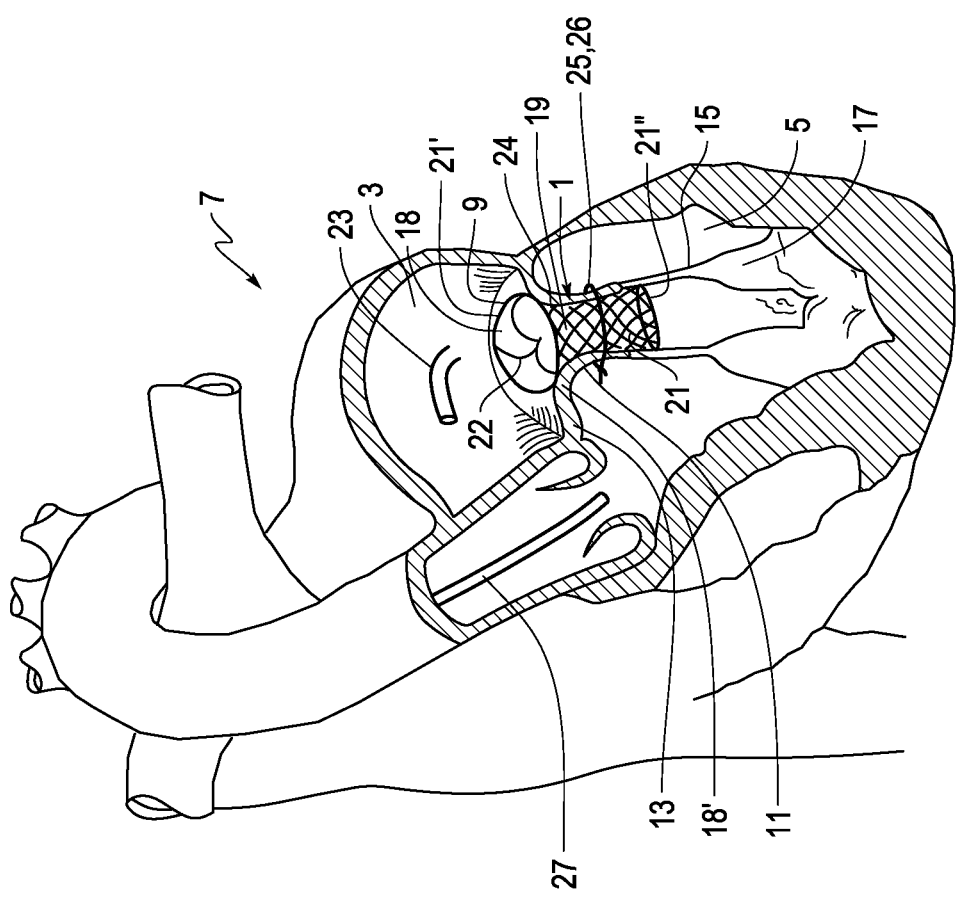
FIG. 1 shows a schematic perspective view of a transcatheter atrio-ventricular valve prosthesis according to an embodiment of the invention.

Implantation of a transcatheter atrio-ventricular valve prosthesis (mitral valve or tricuspid valve prosthesis) on a beating heart can be achieved by a minimally invasive approach in a mammal. This specification describes procedures and apparatuses, including the valve prosthesis itself, to insert and deploy the valve prosthesis and to anchor it by attachment to locations inside the heart.

According to an embodiment, the invention provides a transcatheter atrio-ventricular valve prosthesis. According to another embodiment, the invention provides a method for implanting a transcatheter atrio-ventricular valve prosthesis. Further embodiments of the invention are described below.

According to an embodiment of the invention, a transcatheter atrio-ventricular valve prosthesis for functional replacement of an atrio-ventricular valve in a connection channel, having a circumferential connection channel wall structure, between atrial and ventricular chambers of a heart is provided, comprising an inner device to be disposed in the interior of the connection channel, the inner device having a circumferential support structure or circumferential support body which is radially expandable and having a valve attached to the circumferential support structure, and an outer device to be disposed on the exterior side of the connection channel, wherein the outer device at least partly extends around (circumferentially around) the inner device in a radial distance to the inner device, wherein the inner device, for example the circumferential support structure of the inner device, and the outer device form a clamping mechanism for clamping the circumferential connection channel wall structure of the connection channel therebetween.

The circumferential support structure defines an inner channel or inner through opening forming a replacement channel for functionally replacing or re-enforcing the (native) connection channel between the atrial chamber and the ventricular chamber. In the implanted condition, the circumferential support structure, for example, circumferentially and continuously abuts the inner periphery of the circumferential connection channel wall structure. The (new) valve is fixedly arranged in the interior of the circumferential support structure and, thus, within said replacement channel, and is fixedly attached to the circumferential support structure so as to be able to take over and correspondingly replace the function of the native valve, that is, so as to be able to appropriately open and close the replacement channel to appropriately allow blood flow therethrough between the atrial chamber and the ventricular chamber, between which it is (or is to be) implanted.

According to another embodiment of the invention, a transcatheter atrio-ventricular valve prosthesis for functional replacement of an atrio-ventricular valve in a connection channel, having a circumferential connection channel wall structure, between the atrial chamber and the ventricular chamber of a heart is provided, comprising an inner device to be disposed in the interior of the connection channel, the inner device having a circumferential support structure which is radially expandable, and having a valve attached to the circumferential support structure, wherein the circumferential support structure of the inner device is of tubular shape and extends along an axis and has two axial ends, and an outer device to be disposed on the exterior of the connection channel, wherein the outer device at least partly extends around the inner device in a radial distance to the inner device, and wherein the inner and outer devices form a clamping mechanism for clamping the circumferential connection channel wall structure therebetween, wherein the outer device comprises a ring, for extending circumferentially around the circumferential connection channel wall structure, arranged between and in a distance to the axial ends of the inner device, wherein the outer device further comprises an anchor member having one or more anchor parts, such as one or more barbs and/or one or more hooks, to penetrate into the circumferential connection channel wall structure at a position at or close to the ring, the anchor member comprising an eye, through which the ring extends to thereby be anchored on the circumferential connection channel wall structure at this position by the anchor member.

The (native) connection channel between the native arterial and ventricular chambers (which may be the left chambers in case of (functional) mitral valve replacement or right chambers in case of (functional) tricuspid valve replacement) is defined by the circumferential and/or peripheral connection channel wall structure provided by (the tissue of) the native valve leaflets, the native valve annulus of the native atrial-ventricular valve and, in an embodiment, may also be the adjacent muscular tissue, the generally circumferential chord structure (chordae tendinae) between the valve leaflets and the generally circumferential papillary muscle(s), and said papillary muscle(s), wherein the inner and outer devices are provided such as to (at least partly) circumferentially clamp said connection channel wall structure therebetween. In the area of the native valve leaflets and the native valve annulus, the circumferential connection channel wall structure forms a substantially closed circumferential connection channel wall, and in the area of the chordae tendinae the circumferential connection channel wall structure forms a longitudinally slotted and, hence, more radially opened circumferential wall structure. The inner device is, for example, to be arranged within the circumferential connection channel wall (formed by the valve annulus and the leaflets), thereby achieving an improved sealing and fixation function. Also the outer device is, for example, to be arranged around the mentioned circumferential connection channel wall (formed by the valve annulus and the valve leaflets), and/or the outer device may also be arranged around the circumferential connection channel wall structure in the area of the chordae tendinae and/or in the area of the papillary muscle(s) in as far as the inner device extends into between these/this area(s). According to a further extended approach, part of the respective atrium, for example that part of the respective atrium which is adjacent to the corresponding atrio-ventricular valve to be functionally replaced, may be considered to also form part of the corresponding connection channel so that according to this extended approach the (native) circumferential connection channel wall structure which is to be clamped between the outer and inner devices is formed by a part of the corresponding atrium wall. In this respect, the outer device may also be arranged around the corresponding atrium.

The transcatheter atrio-ventricular valve prosthesis is preferably collapsible to fit inside a delivery catheter and re-expandable to be functional inside the heart cavity. In this respect, the circumferential support structure of the inner device can be brought in a collapsed condition to be then implanted in percutaneous manner, and can then be expanded when being in its final implanted position within the (native) connection channel. The circumferential support structure can be a stent-like component, and can be, for example, self expandable or balloon expandable. It can be made of nitinol or stainless steel or any material enabling properties desired for the application (e.g., biocompatibility, elasticity, yield strength, fatigue resistance, corrosion resistance). It can be laser-cut or assembled from a wire, or produced by other methods. For example, the circumferential support structure can be formed by a mesh-like wire structure of either a shape-memory material, such as nitinol, thereby forming a self-expandable mesh structure, or of a non-shape-memory material, such as stainless steel, thereby forming a non-self-expandable mesh structure which has to be expanded by an additional or separate expanding means, such as by an internal and expandable balloon which is inserted into an interior of the initially collapsed circumferential support structure and which can be inflated and deflated to expand the circumferential support structure and to be then removed therefrom, respectively.

Further, the circumferential support structure is, for example, of a tubular shape (for example, of a tubular mesh shape) which is collapsible and re-expandable to its tubular shape.

The expandability and corresponding collapsibility of the circumferential support structure (the valve attached thereto is correspondingly collapsible and deployable) allows delivery of the inner device by means of a catheter forwarded to the atrio-ventricular valve, for example, via the corresponding atrial chamber or ventricular chamber.

The outer device can also be forwarded by means of a catheter to the atrio-ventricular valve, for example via the atrial chamber or the ventricular chamber, wherein the inner and outer devices may be forwarded simultaneously or one after another via a respective (other) one of the atrial and ventricular chambers or via the respective same of the atrial and ventricular chambers.

The (new, replacing or non-native) valve attached to the circumferential support member can be made of biological tissue, for example, of pericardium, or it can be an artificial valve made of a synthetic material, such as of a plastic film material, for example a PE film material. The non-native valve may be provided as a flap valve arranged in an interior of the circumferential support structure of the inner device, and having one or a plurality of (co-acting) flaps.

When the circumferential support structure is in its finally implanted position, for example between the native valve leaflets and/or the native valve annulus, and will be expanded, the circumferential support structure radially and inwardly contacts against the inner periphery of the circumferential or peripheral connection channel wall structure, for example against the inner periphery of the connection channel wall formed by the native valve annulus and the native valve leaflets. In this respect, the circumferential support structure may be expandable to merely (in general) abut against the inner periphery without causing inner pressure as such. In this case, the active clamping action can be caused by an outer device which is a contractible device and which then can radially and inwardly contract the circumferential connection channel wall structure against the inner device. It is also possible that the outer device is generally not radially contractible, and the clamping force can be actively provided by the inner device, that is, by the expandable circumferential support structure radially expanded to press the (native) circumferential connection channel wall structure against the inner periphery of the outer device. It is also possible that both the inner device, for example its circumferential support structure, and the outer device are expandable and contractible, respectively, such that both provide for such radial forces so as to be able to actively press against the circumferential connection channel wall structure from the inner side and the outer side thereof.

The outer device may be one or more collapsible and correspondingly (re-)expandable or formable, for example circumferentially closed, rings or tubular members, for example in form of one or a plurality of snares, which extend around, for example completely around, the (circumference of the) inner device and can be arranged around, for example completely around, the native connection channel and, hence, the outer circumference of the corresponding circumferential connection channel wall structure. Accordingly, by using a ring, the clamping mechanism can continuously (that is, without interruptions) circumferentially clamp the connection channel wall structure. The outer device may be a closed ring (as shown in e.g., FIGS. 1 and 15) or circumferentially closed tubular member or may be formed as a clamp, for example, as a circumferentially open ring or tubular member (that is, a ring that is open at its circumference such as, for example, a C-shaped ring or a U-shaped ring, or a helix, or a tubular member that is open at its circumference along its longitudinal direction, such as a tubular member having a C-shaped or U-shaped cross-section). Further in this respect, circumferentially open ring or tubular member means that the corresponding (circumferential) free ends of the open ring or tubular member are not connected to each other (are not interconnected) and, hence, are provided connection-free or locking-free. An example of an open helical outer device is shown in FIG. 16. The outer device needs to be deformable, for example collapsible, to also allow delivery thereof by means of a catheter in a percutaneous manner. In the event of an outer device shaped as a tubular member, whether eventually closed or open, it can be made of a material inflatable through a lumen in the delivery catheter, especially in order to take a certain shape or size. It can further be inflated with a material that can be injected in a liquid state and that can be turned into a solid, non deformable component. This can be achieved for instance with a polymer hardening over time or by further addition of energy (for example, heating, ultrasound, UV light or other electromagnetic radiation) or a hardening, drying or reticulating agent. Alternatively, or in addition, the outer device can be made tubular in order to be delivered while positioned over the delivery catheter rather than inside the delivery catheter's lumen. This could then enable delivery of a fastening mechanism (clip, screw, suture . . . ) from the inside of the delivery catheter to the inner side of the tubular outer device. This fastening mechanism could perforate the tubular outer device so as to enable attachment of one end of the outer device to the other end or of an area of the outer device to the anatomy (connection channel wall structure) or to the inner device.

A wire, which may also be a ribbon or a rope, may be used as material for the outer device, the wire forming the above-mentioned ring around the circumferential connection channel wall structure. The wire or wire material may be flexible and non-elastic, but may also be flexible and elastic so as to be able to always provide an elastic clamping force against the inner device.

In general, the outer device may be non-elastically contractible up to any appropriate inner diameter, or the outer device may be elastically contractible up to an inner diameter which, for example is equal or smaller than the outer diameter of the inner device, so as to ensure an elastic clamping force against the circumferential connection channel wall structure when being implanted.

The wire or wire material as such may be linearly forwarded to the atrio-ventricular valve through a catheter and may be wound circumferentially around the outer periphery of the circumferential connectional channel wall structure to form the outer device in the shape of one or more rings such as snare rings. Such rings may be arranged in a respective distance to each other along an axial extension of the inner device along the direction of the connection channel/through opening formed by native atrio-ventricular valve. The wire ring can be easily further contracted to correspondingly contract the connection channel and circumferential connection channel wall structure radially inwardly against the inner device and the circumferential support structure thereof. Thereby, a tight and thereby sealed and reliable circumferential connection between the circumferential support structure with the (new/replacing) valve attached thereto and the inner periphery/circumference of the circumferential connection channel wall structure can be achieved. In this respect, as mentioned above, the inner device with its circumferential support structure may be arranged within the native valve annulus or at an interior position close thereto and in-between the native valve leaflets, and the outer device may be arranged around the exterior of the native valve leaflets close to the native valve annulus to thereby circumferentially and tightly clamp the native valve leaflets, which form part of the connection channel and, thus, of the connection channel wall structure thereof, between the inner and outer devices, thereby providing for safe and reliable seal as well as fixation functions. As mentioned above, the inner device and/or the outer device may also and/or additionally be provided on the inner and outer, respectively, peripheries of further elements of the circumferential connection channel wall structure, such as within and around, respectively, the periphery of the chordae tendinae, the periphery of the papillary muscle(s), and the periphery of the atrial wall.

The outer device, for example the ring, such as the wire ring or ribbon ring, may be of a shape-memory material (e.g., Nitinol) so as to be able to create a contracting force around the native leaflet and inner device, without requirement of any externally applied cinching force. The shape memory material can be characterized by its transition temperature (Af temperature) separating the cold, deformable state (martensitic phase) from the warm state (austenitic phase) where the component springs back to its original shape. The Af temperature of the shape memory material could be set in such a range (e.g., between 40° C. and 60° C.) that the outer device is inserted into position in the anatomy in its cold, deformable state (martensitic phase) so as to enable delivery through the tortuosities of the vasculature and adequate positioning without resistance. It could then be heated beyond the Af temperature, for instance by an electric current, so as to conform to its original shape in its warm state (austenitic phase). Its original shape could be set in such a way that upon recovering this shape after cold deformation and upon heating, a freeze mechanism like a ratchet or anchoring becomes active for instance enabling the two ends of the outer device to become connected. This feature would enable the outer device to maintain its shape and position despite partially cooling down again after the heating action is stopped.

The inner device and the outer device may be separated from each other and may be not in a physical contact with each other. However, the inner and outer devices may also include projections projecting toward each other and penetrating the tissue of the circumferential connection channel wall structure clamped in-between, wherein the penetrating projections of the inner and outer devices may come in contact with the respective other one of the inner and outer devices.

The inner device, for example its circumferential support structure, extends along an axis along the through opening therethrough (following the direction of the native connection channel or through opening through the native atrio-ventricular valve), and the outer device, for example provided as a ring, may be arranged at a position along said axis, that is between the axial ends of the inner device, for example between the ends of the circumferential support structure, to thereby be arranged in a distance (axial distance) from these ends. The inner device, for example its circumferential support structure, may have an elongate shape so that said axis may be the longitudinal axis and the ends may be the longitudinal ends.

The inner and outer devices may also include means for engaging the circumferential connection channel wall structure from the respective inner and outer peripheries thereof. In this respect, the inner device, for example its circumferential support structure, may comprise barbs, hooks, anchor part(s), or other projections for penetrating into the circumferential connection channel wall structure from the interior thereof. Correspondingly, the outer device may include such projections for correspondingly penetrate into the circumferential connection channel wall structure.

On the other hand, the inner device may also be free of projections at or on its outer surface (outer circumferential surface).

Further, the outer device formed by a wire or ribbon may also be at least partially interwoven into the chordae tendinae structure to thereby internally extend therearound, but still in a radial distance to the inner device and its circumferential support structure arranged on the inner periphery of the circumferential connection channel wall structure.

The inner device, for example its circumferential support structure, may be provided with an outer circumferential or peripheral indentation, for example a groove, for example with a V-shaped or U-shaped cross-section, and the outer device may comprise a closed or open ring engaging the indentation, for example the groove, with the connection wall channel structure clamped therebetween. The width of the groove, for example of the U-shaped groove, may be substantially adapted/substantially correspond to the cross-sectional dimension of the ring (ring wall) or may be slightly greater such as to still allow tissue of the corresponding wall structure portion of the circumferential connection channel wall structure to be pressed into the groove following the groove's cross-section, for example the U-shaped cross-section thereon, and laterally pressed against the lateral walls of the groove, and for example additionally pressed against the bottom/base of the groove, for example pressed against the base and/or laterally pressed against the legs of the U-shaped cross-section. The circumferential groove may be a continuously circumferentially extending groove or may extend circumferentially in an interrupted manner. The groove may be formed by (between) adjacent rips which radially protrude from the outer surface of the inner device (such as from its circumferential support structure) and which circumferentially, for example in a continuous or interrupted manner, extend around the inner device (such as around its circumferential support structure). The groove may also be formed by adjacent rows of separated projections (such as bosses) which radially protrude outwardly from the outer surface of the inner device (such as from the outer surface of the circumferential support structure). The groove may also be formed as circumferentially extending (for example in a continuous manner) recess provided in the otherwise smooth or projection-free outer surface of the inner device (such as of the circumferential support structure).

The inner device, for example its circumferential support structure, may be provided with an outer circumferential projection (rib-like projection) as the outer circumferential indentation, and the outer device may comprise one or two rings arranged adjacent to and (in case of two rings) on opposite (axial) sides of the outer circumferential projection.

The inner device, for example its circumferential support structure, may be provided, on its outer periphery, with a compressible material or a compressible structure (the compressible material/structure may be different from the material of the circumferential support structure), such as a foam material, for example as a coating or coating structure or surface structure/material, wherein the compressible material/structure may be compressed when the prosthesis is deployed in the native heart valve. The outer device may locally compress said compressible material/structure into a compressed state to thereby form a corresponding groove in which the circumferential connection channel wall structure is clamped.

The inner device may further have a funnel shape to approach the funnel shape of the connection channel/through opening through the native valve annulus and native valve leaflets of the atrio-ventricular valve in the area of the native valve annulus.

The implantation procedure may be carried out under various visualization means, such as: angiography, echography (Trans Esophageal Echo, Trans Thoracic Echo, Intra Cardiac Echo), MRI.

The catheter(s) for forwarding the inner and outer devices may, for example, be inserted by any of the following paths for treatment of the mitral valve: 1) over an arterial retrograde approach entering the heart cavity over the aorta, 2) through a venous access and through a puncture through the inter atrial septum (trans-septal approach), 3) over a puncture through the apex of the heart (trans-apical approach) or 4) over a puncture through the atrial wall from outside the heart.

The catheter(s) for forwarding the inner and outer devices may, for example, be inserted by any of the following paths for treatment of the tricuspid valve: 1) over an arterial retrograde approach entering the heart cavity over the pulmonary artery following a surgical access of the later, 2) through a venous access, 3) over a puncture through the apex of the heart (trans-apical approach) or 4) over a puncture through the atrial wall from outside the heart.

A possible access for delivering the outer device, for example the wire, ring or snare, is an arterial access (e.g., the femoral artery through a puncture in the groin). A guide-wire may be advanced over the aorta through the aortic valve inside the left ventricle. Over the guide-wire, a guiding catheter can be advanced. The catheter may be pre-shaped on its distal end with an angle of approximately 90° in such a way that it enables positioning of the guide-wire in the sub-annular groove (the space bellow the mitral annulus and between the ventricular wall and the posterior leaflet). Over the guide-wire and inside the guiding catheter, a second pre-shaped catheter can be advanced that will, upon exiting the guiding catheter, position itself around the posterior leaflet inside the sub-annular groove. Advancing the guide-wire inside that pre-shaped catheter allows it to travel around the posterior and the anterior mitral leaflet. A second lumen inside the guiding catheter (for example in form of a second catheter, or a second catheter) allows positioning of a snare to catch the guide-wire after its loop around the native valve leaflets, whereby the native valve leaflets are caught in a lasso manner.

Optionally a catheter can be threaded over the guide-wire to position an anchor (member) inside the ventricular wall or the annulus close to selected areas like the middle of the posterior leaflet. This anchor (member) allows maintenance of the relative height of the guide-wire so as to avoid grabbing the native leaflet too low. It also allows the apparatus to favor the final position of the stent-valve, that is, the inner device with its circumferential support structure and valve, within the mitral annulus plane close to the posterior wall so as for instance to grab a greater length of the posterior leaflet.

In embodiments, the guide-wire can be exchanged for a different kind of lasso with additional features (e.g., greater contact surface, barbs on its surface, shape memory). In addition, if the custom made lasso does not already provide for it, a stopping device can be advanced so as to close the loop and freeze it at a given circumference optimal for stent-valve anchoring.

The outer device, for example formed as a ring, such as a wire ring or snare ring, may be positioned around the native leaflets in such a way that it wraps those leaflets around the deployed inner device. The ring can be positioned at different heights, wherein a (height) position providing an improved sealing function may be seen to be a position as close as possible to the native valve annulus. In this regard, the native leaflets are used to anchor the atrio-ventricular (mitral) valve prosthesis as well as to achieve peri-prosthetic sealing. Preferably, the ring is inserted around the native valve annulus so as to be positioned above the chordae tendinae to provide an improved sealing function.

The outer device, for example, formed as a ring, such as a wire ring or snare ring, may be fixed into place, and thus remain attached inside the heart upon completion of the implantation of the atrio-ventricular (mitral) valve prosthesis. Alternatively, the wire ring or snare ring may be used to position the native leaflets in a selected area to activate an anchoring mechanism, and may be subsequently removed. That is, in some embodiments, the wire ring or snare ring may be used only during the implantation procedure.

According to an aspect of the invention, the outer device, for example in addition to the ring thereof, may further comprise one or more staples arranged around the periphery/circumference of the inner device and each having a base member arranged in a radial distance to and outwardly of the inner device to clamp the circumferential connection channel wall structure between the base member and the inner device and each having penetration legs for penetrating the circumferential connection channel wall structure and engaging the inner device, for example the circumferential support member thereof, for being fixed thereon and for providing the clamping force between the base member and the inner device.

According to an aspect of the invention, for example in addition to the ring and/or in addition to the staples of the outer device, the outer device may comprise one or more clips arranged around the outer circumference or outer periphery of the inner device and having a U-shape with a base portion and two legs extending from the base portion, one of the legs extending in a radial distance to and outwardly of the inner device, the other one of the legs engaging the inner device, for example by engaging the circumferential support member at an inner peripheral/circumferential side thereof, and the base portion may be arranged at a free front end of the native valve leaflets, whereby the clip(s) (axially) extend around the free front end of the native valve leaflets, and the legs clamp the circumferential connection channel wall structure, formed by the leaflets in this area, and the circumferential support structure together, whereby the circumferential connection channel wall structure (here, the native valve leaflets) is positioned between the one clip leg and the circumferential support member of the inner device.

The above-mentioned clips or staples can be inserted through the leaflets to the inner device (clipping from the 'outside'), or through the inner device to the leaflets (clipping from the 'inside'). In the latter case, the base member of the respective staple is arranged on an inner peripheral side of the inner device, for example of the circumferential support member, and the penetration legs of the staple penetrate the circumferential connection channel wall structure from an inner side to an outer side, with the free end of the penetration legs extending in a radial distance outwards of the inner device therealong or therearound, whereby the circumferential connection channel wall structure is clamped between the free ends of the penetration legs and the inner device.

In case of using the above-mentioned clips and/or staples arranged in angular intervals around the circumference of the inner device, the clamping mechanism can correspondingly clamp in a non-continuous (interrupted) circumferential manner.

As an alternative to the outer device, or in addition to the outer device, the inner device may comprise anchors or hooks fixed to the inner device and extending therefrom to be positioned inside the heart muscle (papillary muscle or ventricular wall) to enable the inner device to further resist the back pressure. In this respect, for example, the outer device may comprise elongate anchor elements which extend from the inner device by a (axial) distance so as to be able to penetrate with free ends thereof into native papillary muscle(s) when the inner device is in a finally implanted position within the connection channel.

Further, the inner device itself may contain components to facilitate its inherent anchoring such as hooks, barbs, an adhesive surface (e.g., biological glue), arms or cuffs to wrap around the native leaflets or the chordae tendinae or combinations thereof. According to an aspect of the invention, for example in addition to the ring and/or in addition to the staples and/or in addition to the clips, the outer device may comprise one or more arms extending at the outer periphery of the inner device in a radial distance thereto, to thereby be able to clamp the circumferential connection channel wall structure radially between the arm(s) and the inner device, the arms, starting from a free end thereof, (axially) extend in parallel to the inner device (for example, the circumferential support structure thereof) to thereby form a corresponding radial gap therebetween for receiving the circumferential connection channel wall structure therein for being clamped, and extend towards the inner device (for example, the circumferential support structure thereof) to be connected thereto, for example at an axial end of the inner device (e.g., of the circumferential support structure thereof). Thereby, the arms distributed around the outer periphery of the inner device form a collar therearound for radially wrapping the free ends of the native valve leaflets and for radially clamping the (free ends of the) native valve leaflets in the radial gap between the radial inner side of the collar and the inner device (for example the circumferential support member).

FIG. 1 shows a transcatheter atrio-ventricular valve prosthesis 1 according to an embodiment of the invention, implanted between left atrial and ventricular chambers 3, 5 of a human heart 7 to replace the (function of the) native mitral valve 9 as the native atrio-ventricular valve between said left atrial and ventricular chambers 3, 5. The native mitral valve 9 comprises a native valve structure including native valve leaflets 11, a native valve annulus 13, native chordae tendinae 15, and native papillary muscle(s) 17. The native valve annulus 13, the native valve leaflets 11, chordae tendinae 15 and the papillary muscle(s) 17 form a connection channel 18 between the atrial and ventricular chambers 3, 5, and said connection channel 18 has a circumferential connection channel wall structure 18'.

The valve prosthesis 1 of FIG. 1 comprises an inner device 19 with a circumferential support structure 21 in form of an elongate tubular mesh-like body, within which a valve 22 in form of a three-flap structure is arranged and attached/fixed, for example non-detachably attached, to the circumferential support structure 21. The (new) valve 22 and, hence, its flap structure is provided such as to close a replacement connection opening/replacement connection channel provided through or interiorly defined by the circumferential support structure 21, here along the longitudinal axis of the circumferential support structure 21, when the left ventricular chamber 5 is contracted, and to open said replacement connection channel when the left ventricular chamber 5 is expanded. In this case, the inner device 19 with its circumferential support structure 21 and its valve 22 therewithin is arranged in-between the native leaflets 11 as well as within the native valve annulus 13 and, thus, within the (native) connection channel 18 in physical and circumferential contact with the inner side of the circumferential connection channel wall structure 18' thereof.

The circumferential support structure 21 is radially compressible to thereby be insertable into the mitral valve 9 by means of a catheter 23 via a percutaneous approach. When in place in the interior of the connection channel 18, the circumferential support structure 21 is brought from its collapsed condition into a deployed condition circumferentially abutting, for example pressing, against the inner periphery of the circumferential connection channel wall structure 18' of the connection channel 18 of the native atrial valve 9, here against the inner periphery of both the native valve leaflets 11 and the native valve annulus 13.

The valve prosthesis 1 further comprises an outer device 25 in form of or comprising a wire ring 26 or snare ring 26 disposed on and extending completely around an exterior or outer side of the connection channel 18 and of the circumferential connection channel wall structure 18' thereof, here, around the native valve leaflets 11 at a position close to the valve annulus 13 and between longitudinal ends of the circumferential support structure 21 of the inner device 19. In this embodiment, the outer device 25 is separate from the inner device 19 and is not in physical contact therewith. The ring-shaped outer device 25 thereby circumferentially extends around the inner device 19 in a radial distance thereto, wherein the circumferential connection channel wall structure 18', here the circumferential connection channel wall formed by the native valve annulus 13 and the native valve leaflets 11, is clamped between the inner and outer devices 19, 25 which thereby form a clamping mechanism for continuously circumferentially clamping the connection channel wall structure 18' therebetween.

The wire ring 26 of the outer device 25 may be elastically or non-elastically contractible so as to be able to add additional active clamping force from radially outside of the valve structure 11, 13, 15, 17 thereagainst. The wire material of the wire of the outer device 25 may be linearly forwarded to the exterior of the circumferential connection channel wall structure 18' via a catheter 27 forwarded via a percutaneous approach.

As can be further seen in FIG. 1, the elongated tubular shaped circumferential support structure 21 of the inner device 19 extends along a (longitudinal) axis which in turn extends along the longitudinal axis of the connection channel 18 (axis extending across to the through opening between the atrial chamber 3 and the ventricular chamber 5), whereby the circumferential support structure 21 correspondingly has (two) axial ends 21', 21". At one of the axial ends 21', 21", which is proximal to the native valve annulus 13, the circumferential support structure is formed in a funnel shape (defining a funnel portion 24) to approach the native funnel shape of the connection channel 18 in the area of the native valve annulus 13. The ring-shaped outer device 25 is arranged at a (an axial) distance from the axial ends 21', 21" therebetween and, thereby, at an axial distance from the funnel portion 24.

In FIGS. 2A to 2E an approach for implanting the prosthesis 1 according to FIG. 1 will now be explained.

Figure 2A:
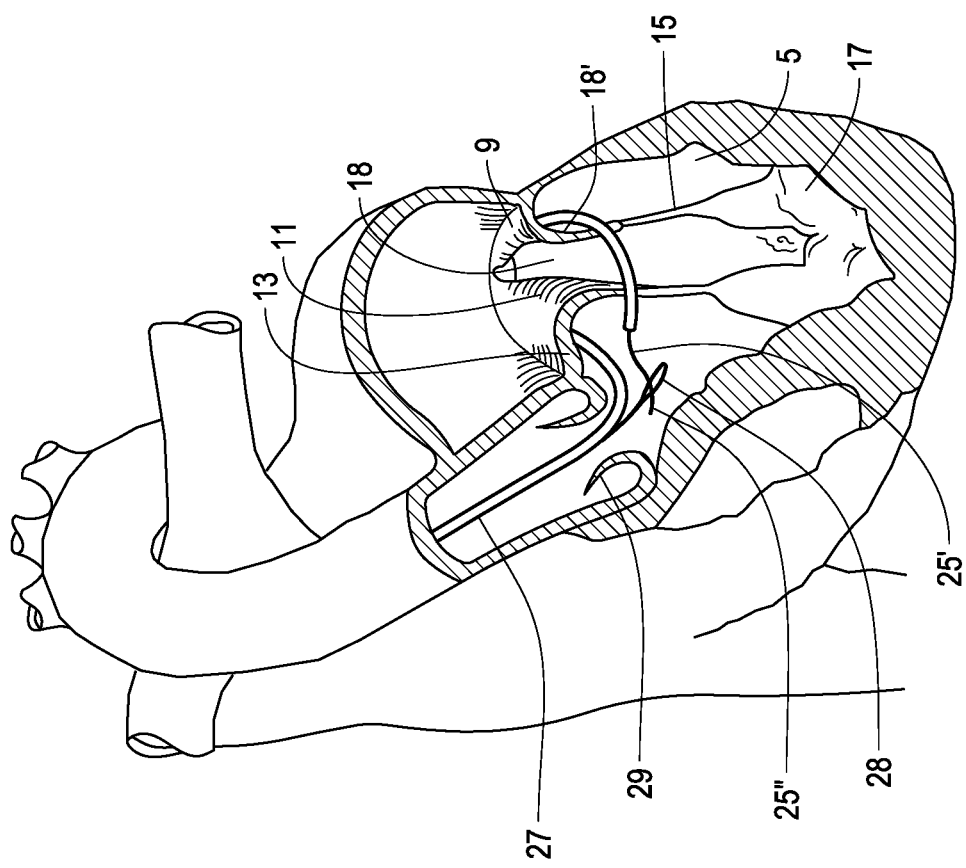
FIGS. 2A-2E show steps of an implantation approach for implantation the prosthesis according to an embodiment of the invention.
Figure 2B:
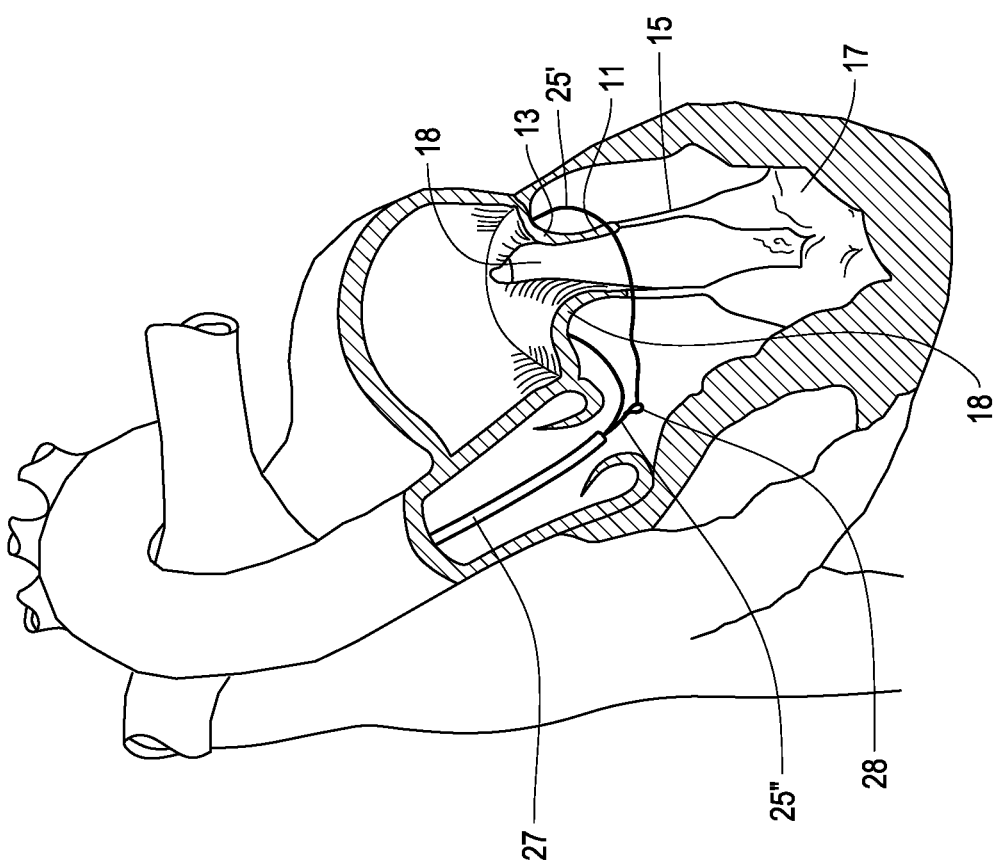
Figure 2C:
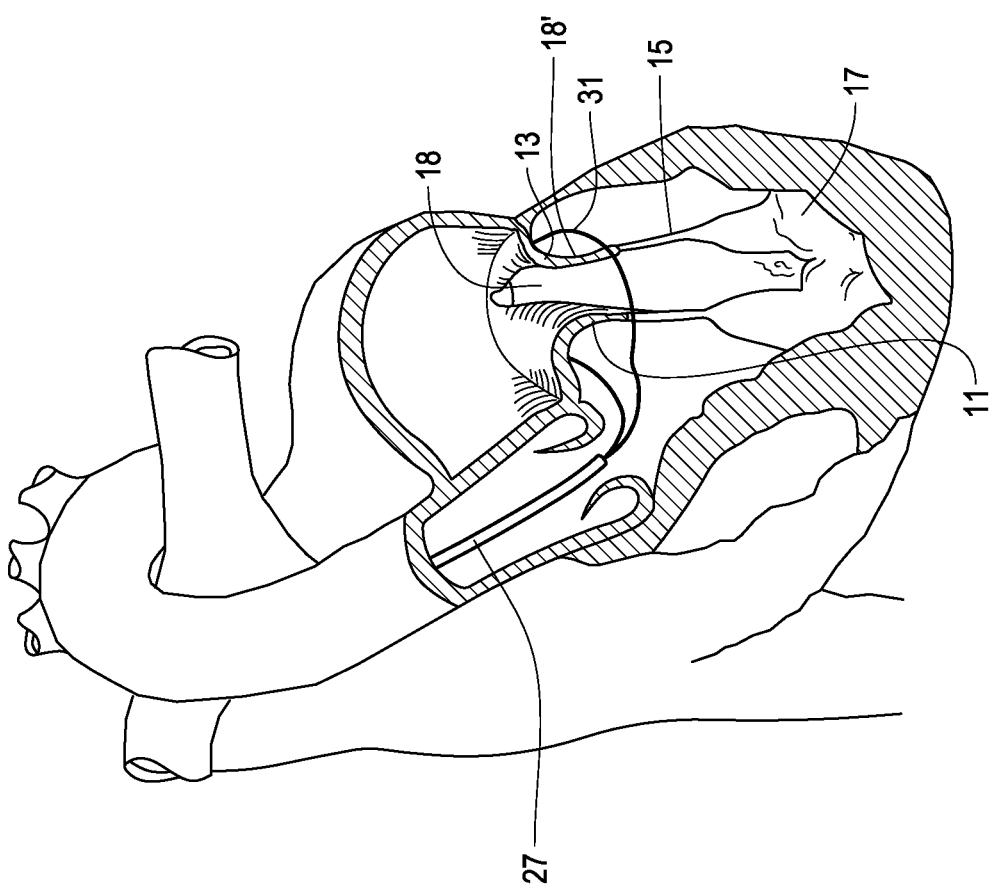

As can be seen from FIGS. 2A to 2C, firstly the catheter 27 is forwarded to the left ventricular chamber 5 via the aorta and the aorta valve 29, and is then guided around the circumferential connection channel wall structure 18' of the connection channel 18, at the level (height) of the native valve leaflets 11 close to the native annulus 13, of the mitral valve 9 to be functionally replaced by the prosthesis 1. That is, the catheter 27 is guided around the circumferential connection channel wall structure 18' of the connection channel 18 and not around the chordae tendinae, which could otherwise undesirably result in the ring-shaped outer device 25 being caught on or placed between chordae tendinae. A flexible and non-elastic wire 25' which will form the ring 26 of the outer device 25 is guided through the catheter 27 and, thereby, is guided around the outer circumference of the circumferential connection channel wall structure 18' at the corresponding level of the native valve leaflets 13. The catheter 27 is then slightly retracted and the wire 25' is then provided as contractible loop 31 (lasso type) having a diameter greater than the (cross-sectional) outer diameter of the circumferentially extending connection channel wall structure 18' and greater than the diameter of the final ring 26 of the outer device 25. The loop 31 thereby extends around the connection channel 18 at a radial distance thereto, that is, at a radial distance to the connection channel wall structure 18', and allows the inner device 19 to be appropriately inserted into the inner side/interior of the connection channel 18.

In order to catch the free end 25" of the wire 25' and to thereby form the loop 31, a catching wire or additional lasso wire, having a contractible catching snare 28 at its distal end, is forwarded through the catheter 27. By means of said snare 28 of the catching wire the free end 25" of the wire 25' is caught and drawn into the catheter 27 to thereby form the loop 31 formed by the wire 25', which loop then can be further contracted to closely circumferentially engage the connection channel wall structure 18'. Instead of the shown snare 28, a catching basket (not shown) may be used for catching the free end 25" of the wire 25', which is provided on the snare or lasso wire. Such a catching basket may, for example, be formed as a tubular member provided with longitudinal slots, wherein the tubular member can be axially contracted to laterally widen the longitudinal slots, in order to receive the free end 25" within one or more of the longitudinal slots, and can be axially re-extended (after axial contraction) to thereby laterally narrow/close the previously widened slots to thereby catch/fix the free end 25" of the wire 25' therein. It is to be noted that other catching mechanisms/catching devices may be used, instead of the catching snare or catching basket, to catch or grip the free end of the wire 25", such as any gripping device, such as a gripper device or forceps.

Figure 2D:
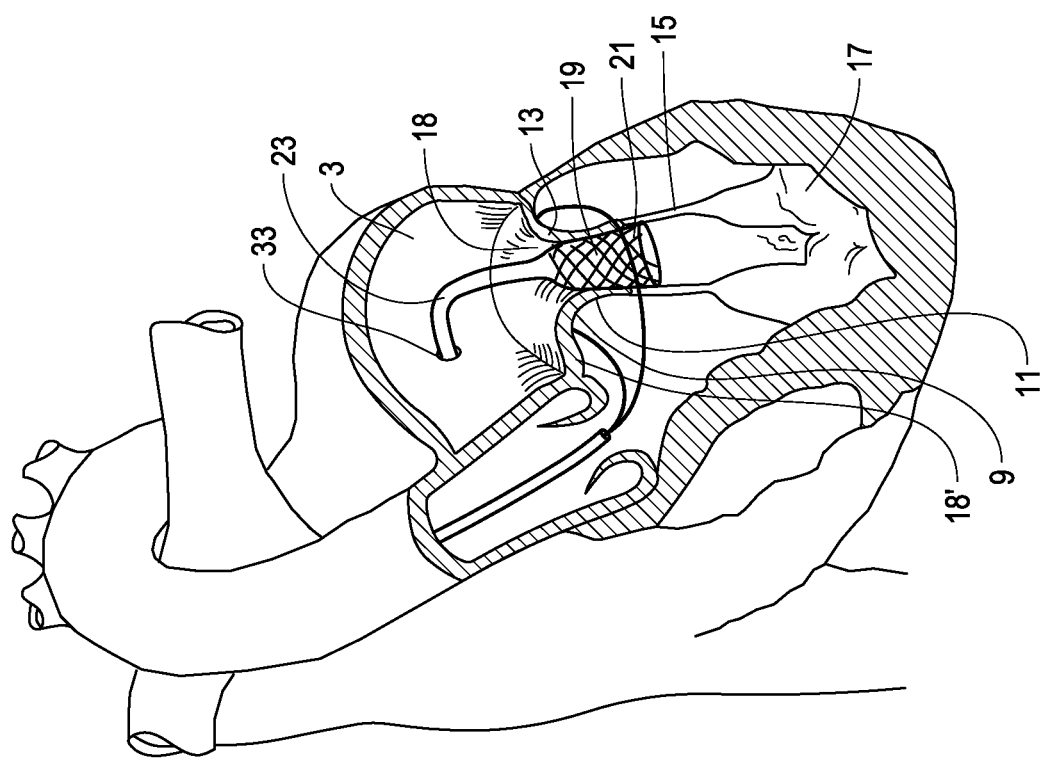
Figure 2E:
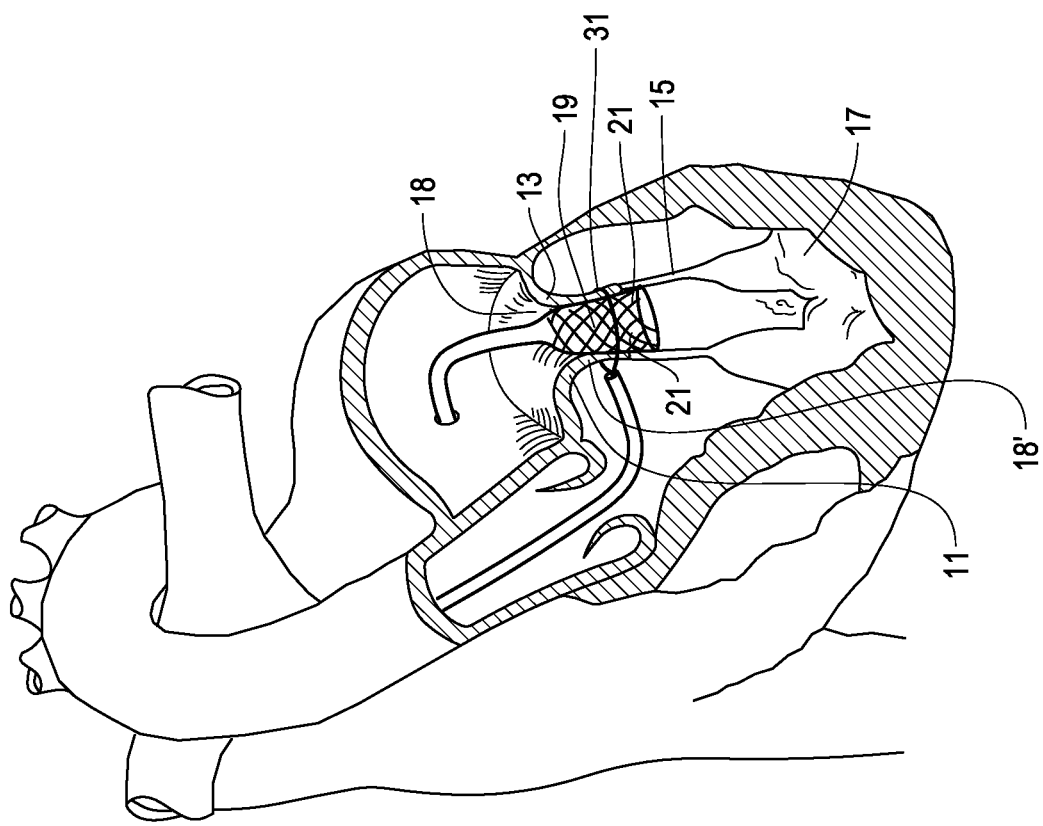

As can be seen from FIG. 2D, the catheter 23 is then forwarded to the left atrial chamber 3 via a puncture 33 through the inter atrial septum, and the inner device 19 with its circumferential support structure 21 and the (new or replacing) valve 22 therein is forwarded in its collapsed condition through the catheter 23 to be disposed in-between the native leaflets 11 and the native annulus 13 forming part of the connection channel 18. Then the circumferential support structure 21 is deployed by either radial self-expansion or radial expansion by means of, for example, an inflatable balloon inserted into the interior of the circumferential support structure 21, whereby the circumferential support structure 21 radially and outwardly presses against the inner periphery of the circumferential connection channel wall structure 18' in the area of and at the level of the native valve annulus 13 and the native valve leaflets 11. As can be seen from FIG. 2E, the loop 31 is then contracted to provide a radial counter-force against the radial force provided by the inner circumferential support structure 21, acting radially and inwardly against the circumferential outer periphery of the circumferential connection channel wall structure 18' at a level of the native valve leaflets 11 adjacent to the native valve annulus 13. Thereby, the connection channel wall structure 18' of the connection channel 18 and, for example in this case, the native valve leaflets 11 and the native valve annulus 13, is prevented from being inappropriately radially expanded and is circumferentially clamped in-between the circumferentially extending loop 31 and the circumferential support structure 21 of the inner device 19. Finally the diameter of the loop 31 is fixed to thereby finalize the ring 26 forming the outer device 25 in this case, and thereby finalizing the implantation of the atrio-ventricular (here mitral) valve prosthesis 1 as shown in FIG. 1.

In sum, with respect to FIGS. 2A-2E, the loop 31 is first positioned around the native valve annulus 13. Afterward, the inner device 19 with its circumferential support structure 21 and the valve 22 therein is forwarded in its collapsed condition through the catheter 23 to be disposed in-between the native leaflets 11 and the native annulus 13 forming part of the connection channel 18. Next, the loop 31 is tightened to pull the native leaflets 11 toward the inner device 19, which is expanded from the collapsed condition. The loop 31 can then either be frozen in position and then removed once the inner device 19 is secure, or the loop 31 may be non-frictionally employed to position the inner device 19 and allow another form of anchoring to be activated, and then the loop 31 is subsequently removed.

Figure 3:
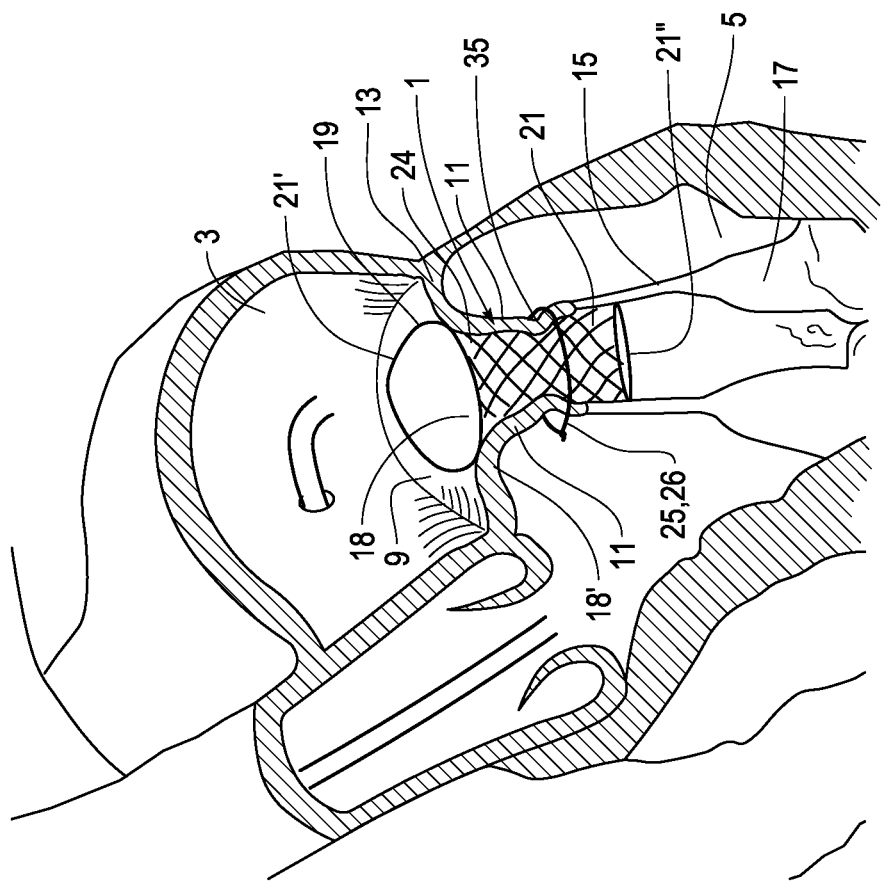
FIG. 3 shows a schematic perspective view of a transcatheter atrio-ventricular valve prosthesis according to another embodiment of the invention.

FIG. 3 shows an atrio-ventricular valve prosthesis 1 according to another embodiment of the invention. According to this embodiment, the circumferential support structure 21 of the inner device 19 is provided with an indentation in the form of an outer circumferential groove 35, and the ring-shaped or snare-shaped outer device 25 is arranged to be (axially) aligned to the outer circumferential groove 35. That is, the ring-shaped outer device 25 is arranged at the level of the outer circumferential groove 35 to thereby force the corresponding area of the native valve leaflets 11 and, hence, the corresponding area of the connection channel wall 18' of the native mitral valve 9 radially into the outer circumferential groove 35 as a result from clamping the said area of the circumferential connection channel wall structure 18' between the outer and inner devices 25, 19. The circumferential groove 35 may allow for a use of the ring-shaped outer device 25 that does not involve frictionally securing the prosthesis in place. That is, the ring-shaped outer device may, upon tightening, be loosely positioned within the circumferential groove 35 to ensure proper positioning of the atrio-ventricular valve prosthesis 1 (see FIG. 15) until the inner device 19 is secured to the circumferential connection channel wall structure 18' with, for example, sutures, staples, barbs, adhesives or another anchor mechanism.

As can be further seen in FIG. 3, the circumferential support structure 21 of the inner device 19 is of an elongated tubular shape and extends along an axis which in turn extends along the longitudinal axis of the connection channel 18 (axis extending cross to the through opening between the atrial chamber 3 and the ventricular chamber 5), whereby the circumferential support structure 21 correspondingly has (two) axial ends 21', 21". At one of the axial ends 21', 21", which is proximal to the native valve annulus 13, the circumferential support structure is formed in a funnel shape (defining a funnel portion 24) to approach the native funnel shape of the connection channel 18 in the area of the native valve annulus 13. The funnel shape of the funnel portion 24 can minimize or prevent one way migration of the circumferential support structure 21 of the inner device 19. The circumferential support structure 21 of the inner device 19 may also have hooks, barbs or some other anchor mechanism that prevents migration of the circumferential support structure 21 of the inner device 19, at least in an opposite direction from that prevented by the funnel portion 24. The ring-shaped outer device 21 and correspondingly the groove 35 aligned therewith are arranged in a distance (axial distance) from the axial ends 21', 21" between the axial ends 21', 21" and, thereby in an axial distance from the funnel portion 24.

Figure 4:
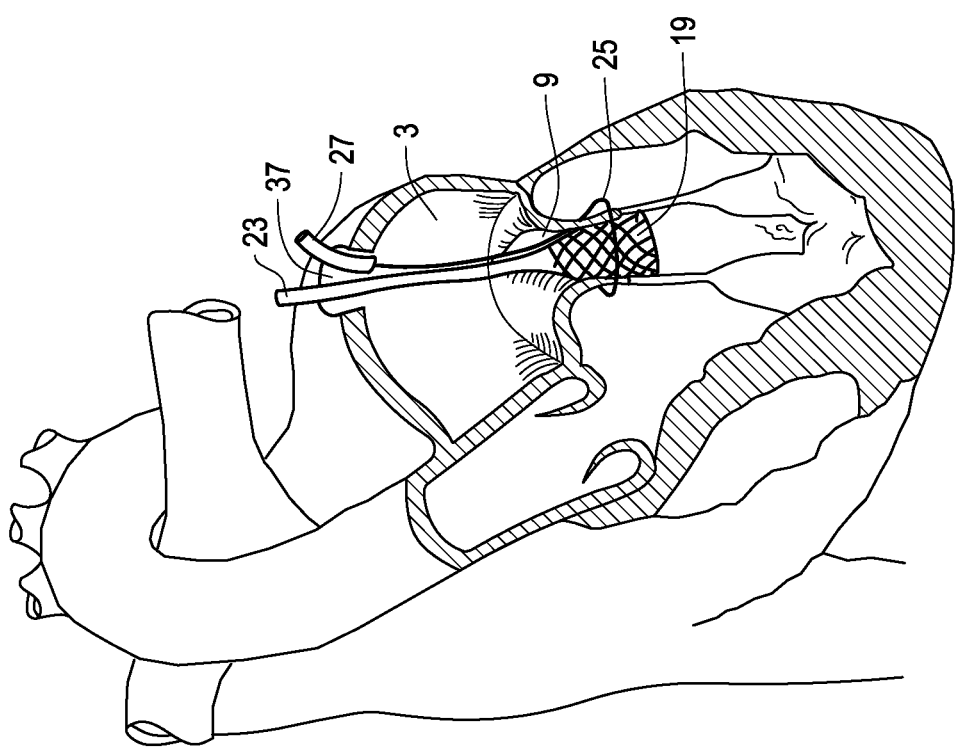
FIGS. 4 and 5 show other implantation approaches for implantation the prosthesis according to an embodiment the invention.

FIG. 4 shows an implantation approach, according to which both catheters 23, 27 for forwarding the inner device 19 and the outer device 25, respectively, are forwarded to the native mitral valve 9 via the atrium 3 and a puncture 37 through the atrial wall from outside the heart. Instead of the puncture 37, the atrium 3 may also be surgically accessed, wherein the access may be carried out on a beating heart or on an arrested heart.

Figure 5:
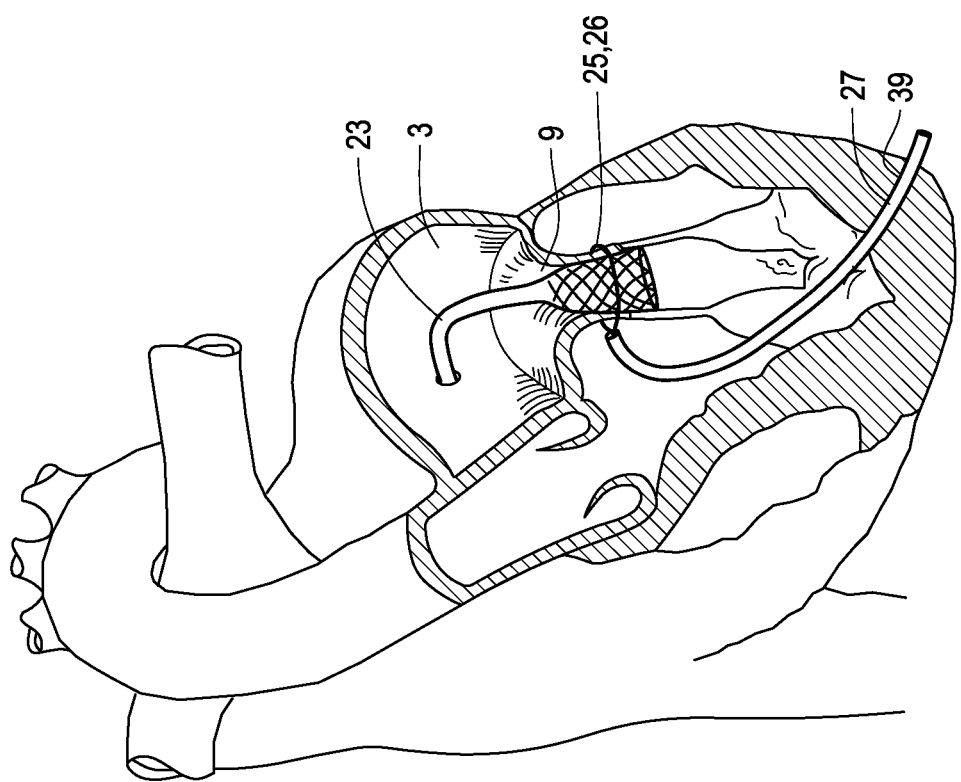

FIG. 5 shows an implantation approach, according to which the catheter 23 for forwarding the inner device 19 to the native mitral valve 9 is forwarded via the left atrial chamber 3, and the catheter 27 for forwarding the outer device 25 to the native mitral valve 9 is forwarded via a puncture 39 through the apex of the heart (trans-apical approach).

Figure 6:
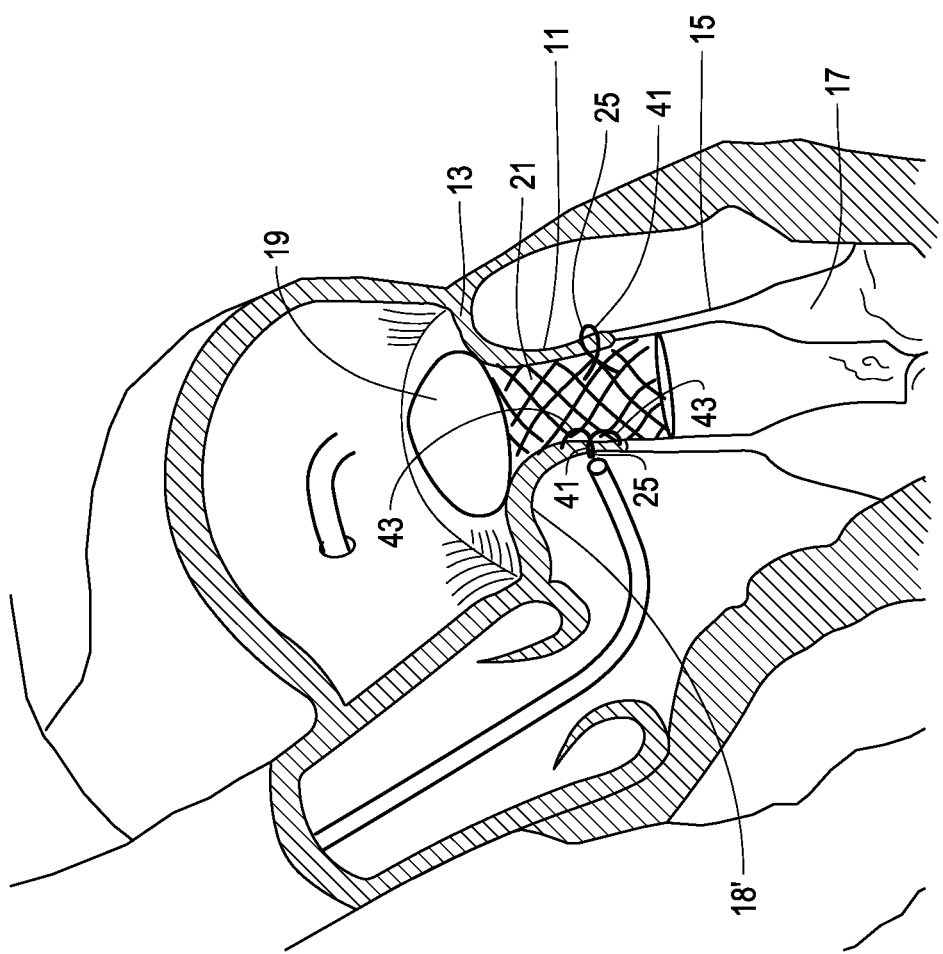
FIG. 6 shows a schematic perspective view of a transcatheter atrio-ventricular valve prosthesis according to another embodiment of the invention.

FIG. 6 shows an embodiment of the invention, according to which the outer device 25, for example in addition to the ring-shaped device 25 of FIG. 1, additionally or only comprises a plurality of staples arranged around the periphery of the inner device 19. The inner device 19 is provided as tubular stent as described in connection with the embodiment of FIG. 1 so that it is referred to the corresponding description above. The respective staple has a base member 41 extending in a radial distance to the circumferential support structure 21 of the inner device 19 at a radial outer side thereof to thereby clamp the circumferential connection channel wall structure 18' (here, the native valve leaflets 15) radially between the base member 41 of the staple and the inner device 19 with its circumferential support member 21 and valve. The radial clamping force is in this case achieved by penetration legs 43 radially penetrating the circumferential connection channel wall structure 18' (here, the native valve leaflets 15) from the outside towards the inside and engaging the mesh-structure of the circumferential support structure 21 to thereby radially and peripherally draw said circumferential support structure 21 towards the respective staple base member 41 with the circumferential connection channel wall structure 18' (here, the native valve leaflets 15) clamped therebetween.

Figure 7:
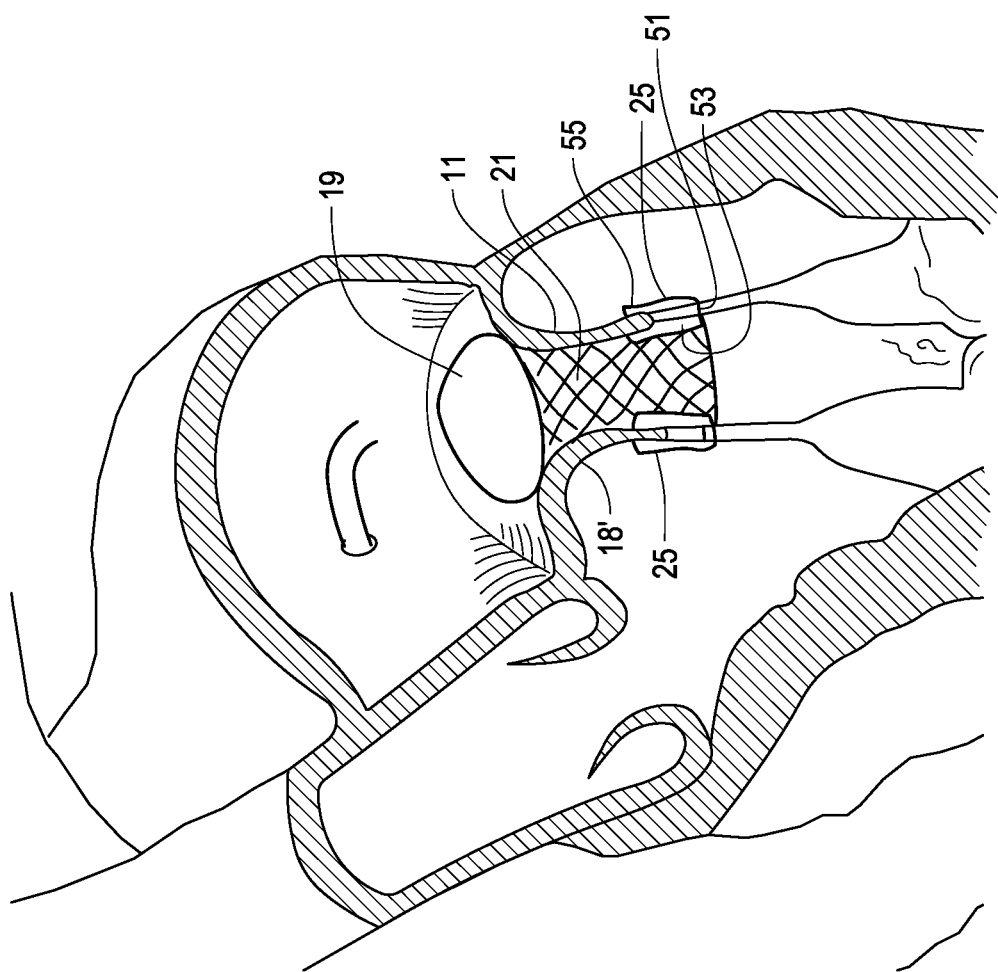
FIG. 7 shows a schematic perspective view of a transcatheter atrio-ventricular valve prosthesis according to another embodiment of the invention.

FIG. 7 shows an embodiment of the invention, according to which the outer device 25, for example in addition to the ring-shaped device 25 of FIG. 1 and/or in addition to the staples of FIG. 6, additionally or only comprises a plurality of clips or clamps arranged around the outer periphery of the inner device 19 at the free ends of the native valve leaflets 11 and at an axial end of the inner device 19. The inner device 19 is provided as a tubular stent as described in connection with the embodiment of FIG. 1 so that it is referred to the corresponding description above. The respective clip is generally of U-shape with a U-base portion 51 and two U-leg portions 53, 55. The clips are arranged such as to respectively encompass the free end of the native valve leaflets 11 and the axial front end of the tubular inner device 19, wherein an outer leg portion 55 of the leg portions 53, 55 extends in a radial distance to the inner device 19 along the axial direction thereof and is in a clamping contact with the radial exterior side of the circumferential connection channel wall structure 18' (here, the native valve leaflets 15), and an inner leg portion 53 extends along the axial direction of the inner device 19 (along the circumferential support structure 21) and is in a clamping contact therewith, whereby the inner device 19 (including the circumferential support structure 21 thereof) and the connection channel wall structure 18' (here, the native valve leaflets 15) are radially clamped between the leg portions 53, 55 of the respective clip.

Figure 8:
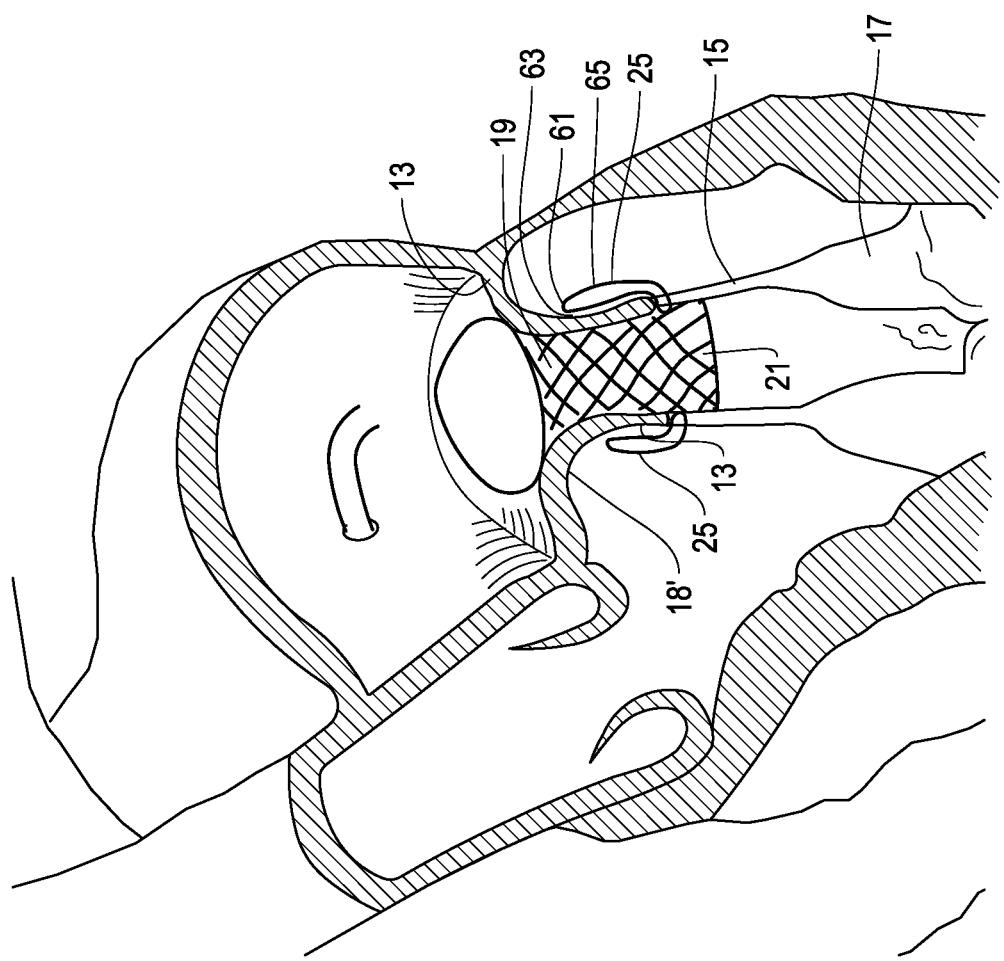
FIG. 8 shows a schematic perspective view of a transcatheter atrio-ventricular valve prosthesis according to another embodiment of the invention.

FIG. 8 shows an embodiment of the invention, according to which the outer device 25, for example in addition to the ring-shaped device 25 of FIG. 1 and/or in addition to the staples and/or clips of FIGS. 6 and 7, additionally or only comprises a plurality of arms extending around the outer circumference/periphery of the inner device 19 in a radial distance thereto, to clamp the circumferential connection channel wall structure 18' radially between the arm(s) and the inner device 19, the arms, starting from a free end 61 thereof, extend in parallel to the inner device 19 (for example, the circumferential support structure thereof 21) to thereby respectively form a corresponding radial gap 63 therebetween for receiving the circumferential connection channel wall structure 18' (here the free ends of the valve leaflets 11) therein for being clamped, and extend towards the inner device 19 (for example, the circumferential support structure 21 thereof) and are fixedly connected to the inner device 19 at an axial end thereof. Thereby, the arms 25 distributed around the outer periphery of the inner device 19 form an angularly interrupted collar 65 therearound for radially wrapping the connection channel wall structure 18' (here, the free ends of the native valve leaflets 13) and for radially clamping the connection channel wall structure 18' (here, the free ends of the native valve leaflets 13) in the radial gap 63 between the radial inner side of the collar 65 and the inner device 19 (for example the circumferential support member 21). The inner device 19 is provided as a tubular stent as described in connection with the embodiment of FIG. 1 so that it is referred to the corresponding description above.

Figure 9:
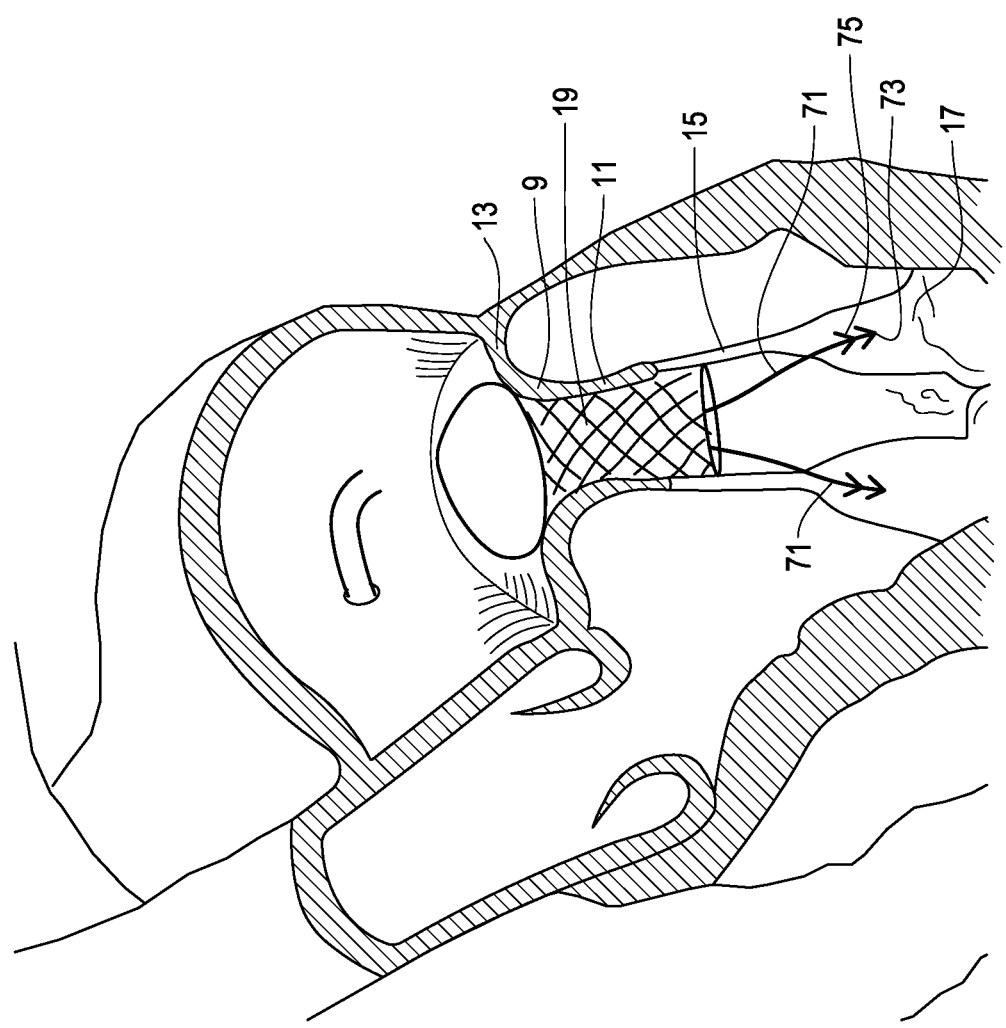
FIG. 9 shows a schematic perspective view of a transcatheter atrio-ventricular valve prosthesis according to another embodiment of the invention.

FIG. 9 shows an embodiment of the invention, according to which in addition to the outer device 25 or, for example, as an alternative thereto, the inner device 19, which is provided as a tubular stent as described in connection with the embodiment of FIG. 1, comprises elongate anchor elements 71, for example in form of elongate wire anchors provided with hooks or barbs 73 at free ends 75 of the anchor elements 71, which anchor elements 71 axially extend from the inner device 19 by a distance so as to be able to penetrate with their free ends 75 into the native papillary muscle(s) 17, when the stent-type inner device 19 is in its finally implanted position within the native mitral valve 9, for example between the native valve leaflets 11 thereof.

In all aspects of the invention, the (new/replacing) valve attached to the circumferential support structure of the stent-type inner device may comprise a circumferential wall portion which is circumferentially and radially clamped as part of the inner device against the inner periphery of the circumferential connection channel wall structure of the native atrial-ventricular valve to thereby provide for further improved seal function between the circumferential connection channel wall structure and the inner device. The outer device may be arranged aligned to or at a level of said circumferential wall portion of the (new/replacing) valve to thereby provide the clamping force at the level of or at least close to said circumferential wall portion of the valve.

Figure 10:
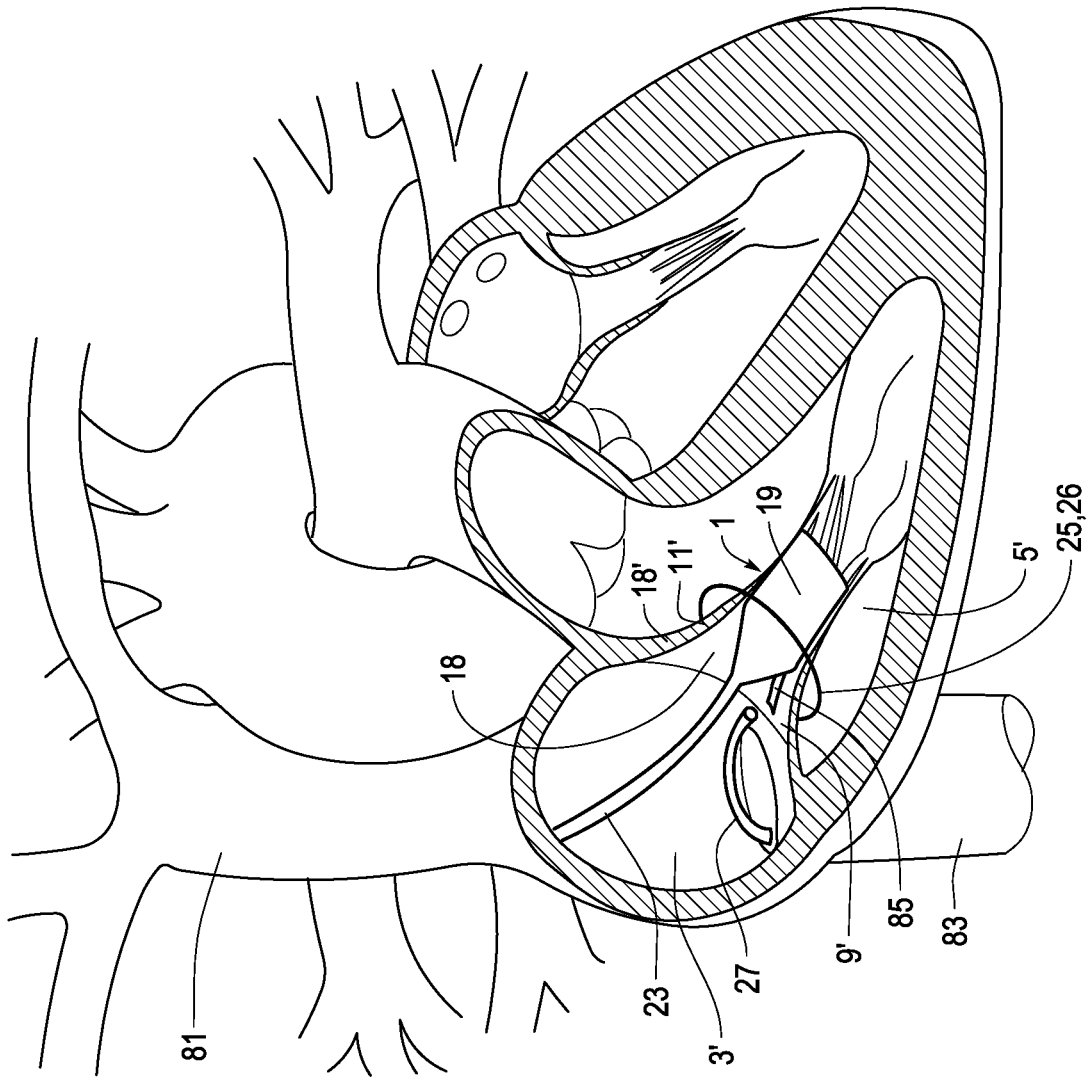
FIG. 10 shows a schematic perspective view of a further approach for implanting a transcatheter atrio-ventricular valve according to an embodiment of the invention.

FIG. 10 shows an approach for implanting a transcatheter atrio-ventricular valve prosthesis 1 within the native tricuspid valve 9' for replacing the function thereof. The prosthesis 1 according to this embodiment is identical to the prosthesis according to FIG. 1 so that regarding the structure of the prosthesis of FIG. 10 it is referred to the description of the embodiment of FIG. 1. The native tricuspid valve 9' defines a connection channel 18, having a circumferential connection channel wall structure 18', fluidly connecting the right atrial and ventricular chambers 3', 5'.

As can be seen from FIG. 10, the inner device 19 is forwarded to the tricuspid valve 9' via the superior vena cava 81, connected to the right atrium 3', by means of a catheter 23, and the outer device 25 is forwarded to the exterior of the connection channel 18, that is to the right ventricular chamber 5' and, thus, to the exterior of the circumferential connection channel wall structure 18', via the inferior vena cava 83 and a passage 85 between the leaflets 11' of the tricuspid valve 9'. Alternatively, the catheter 23 with the inner device 19 may be forwarded via the inferior vena cava 83, and the catheter 27 with the outer device 25 may be forwarded via the superior vena cava 81, or both catheters 23, 27 may be forwarded via the same one of the superior vena cava 81 and inferior vena cava 83. For introducing the catheters 23, 27 into the veins 81, 83 or, in case of a mitral valve prosthesis as described above, into the aorta, femoral, cervical and/or thoracic accesses may be used as appropriate and/or as presently known for other heart catheter applications, such as for the application of known heart catheter probes. Further, the catheter 23 with the inner device 19 may also be forwarded to the tricuspid valve 9' via a puncture (not shown) through the right atrium 3' or via a surgical access to the right atrium 3', which may be carried out on the arrested or beating heart. The catheter 27 with the outer device 25 may also be forwarded via a puncture (not shown) through the right ventricular chamber 5'.

FIG. 11A shows a perspective sectional view of a further embodiment of the invention, and FIG. 11B shows a section along line B-B in FIG. 11A. The embodiment shown in FIGS. 11A and 11B substantially corresponds to the embodiment of FIG. 3, wherein, however, the ring 26 forming the outer device 25 is not a closed ring but an open ring having non-connected or non-interconnected free ends 25', 25" (cf.

FIG. 11B). The ring-shaped outer device 25 is arranged at the (axial) level of the groove 35 provided in and circumferentially extending around the inner device 19 (that is, provided in and extending around the circumferential support structure 21 of the inner device 19). That is, the ring 26 forming the outer device 25 is aligned with the circumferential groove 35. The section, shown in FIG. 11B, extends centrally through and along the groove 35. Regarding the further details of the embodiment of FIGS. 11A and 11B, it is referred to the above explanation of the embodiment of FIG. 3.

FIGS. 12A-12J schematically show an approach for implanting a ring-shaped outer device 25 (cf. FIG. 12) J of a transcatheter atrio-ventricular valve prosthesis 1, as for example described above, according to an embodiment of the invention.

Figure 12A:
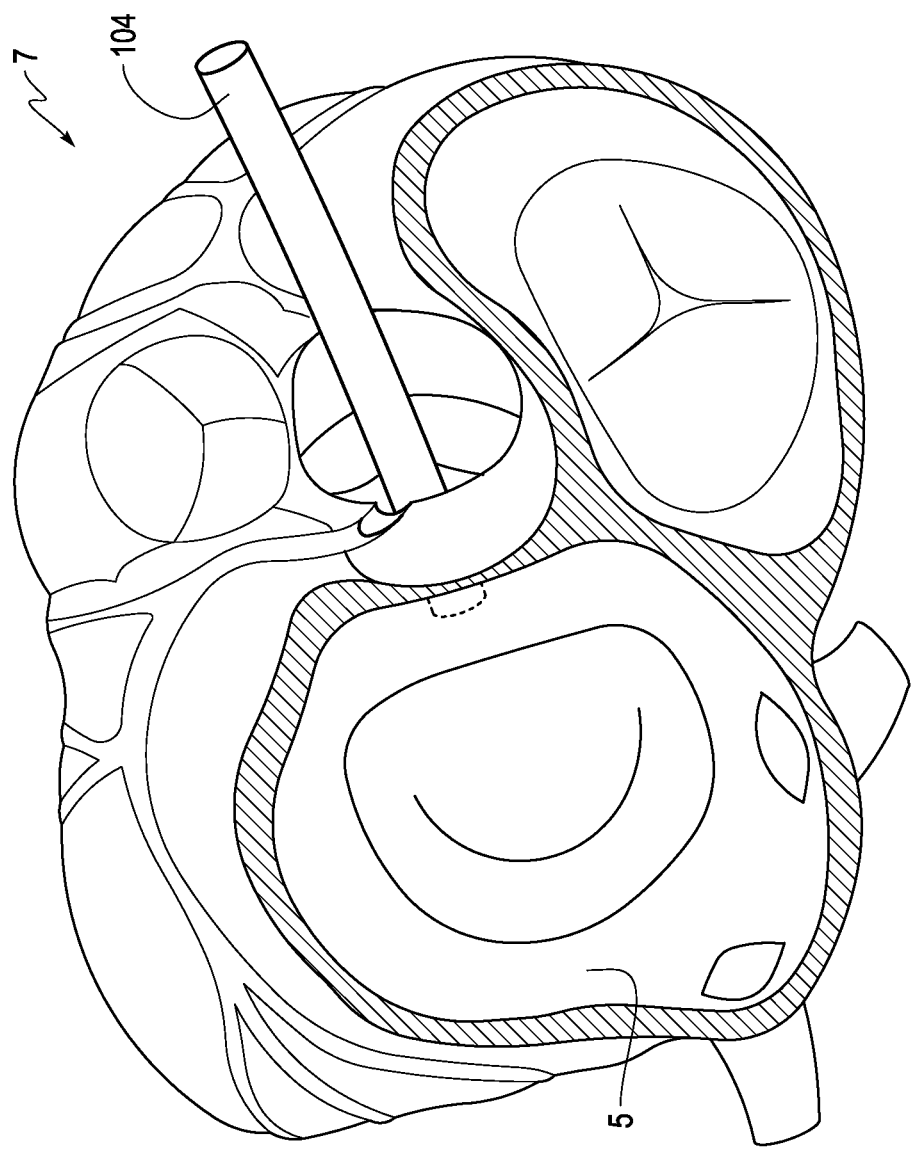
FIGS. 12A-12J show sectional views for explaining an approach for implanting the outer device of the prosthesis according to an embodiment of the invention.
Figure 12B:
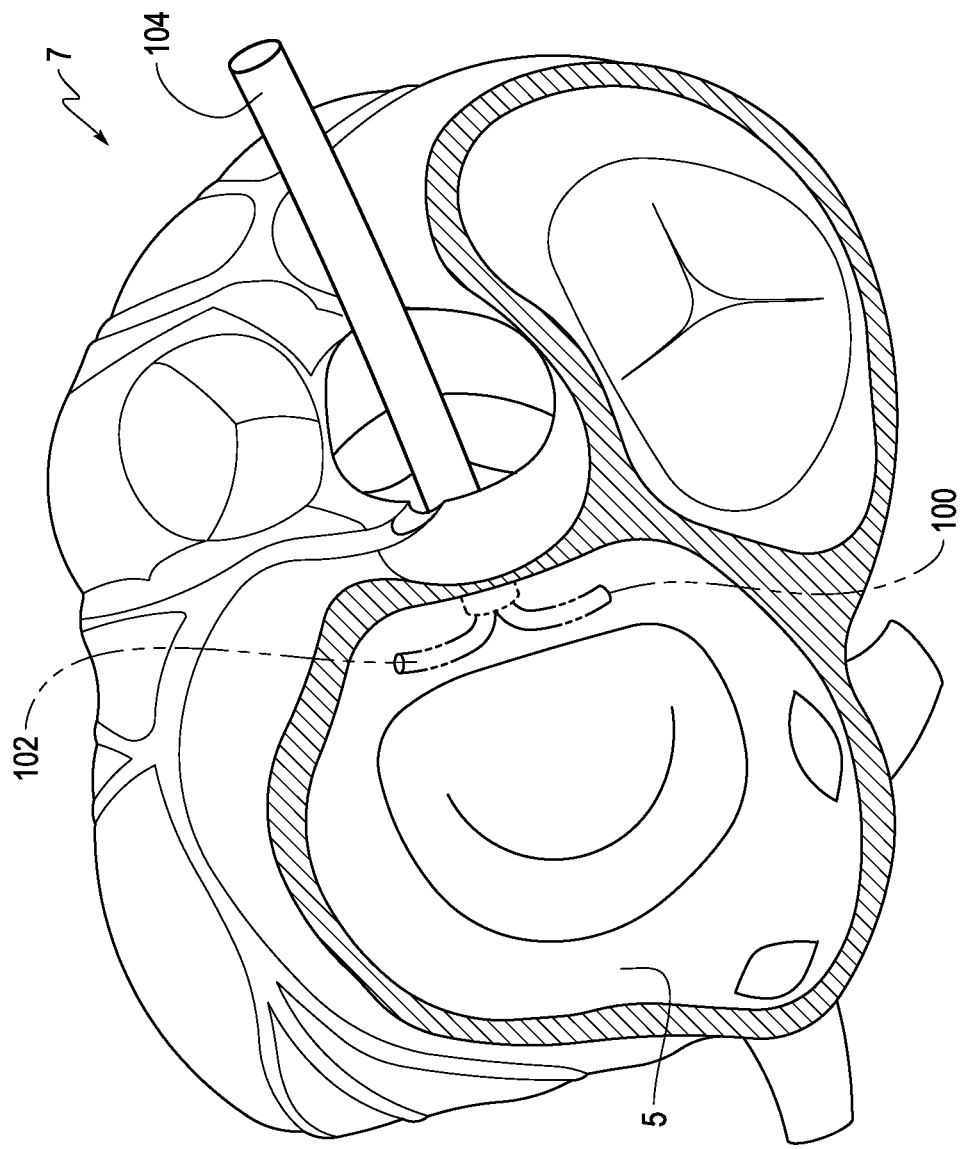
Figure 12C:
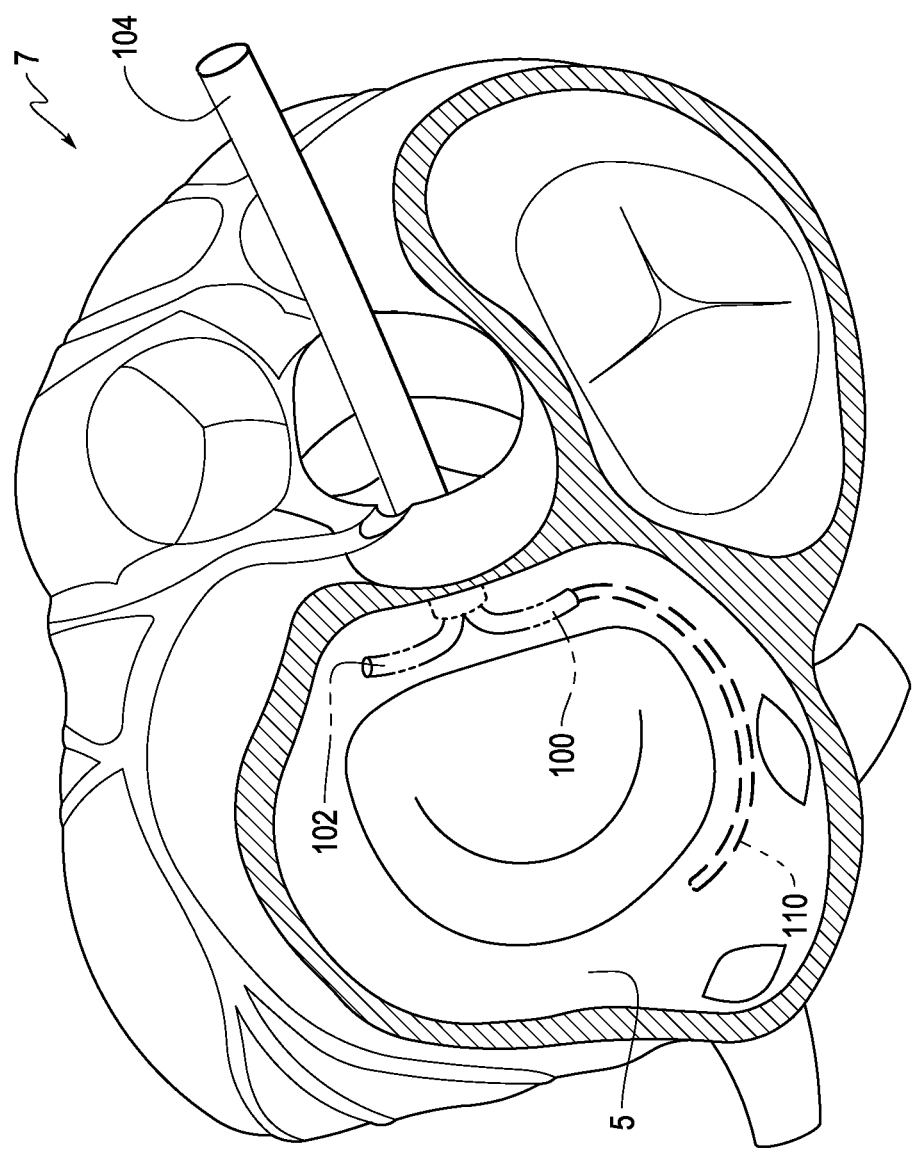
Figure 12D:
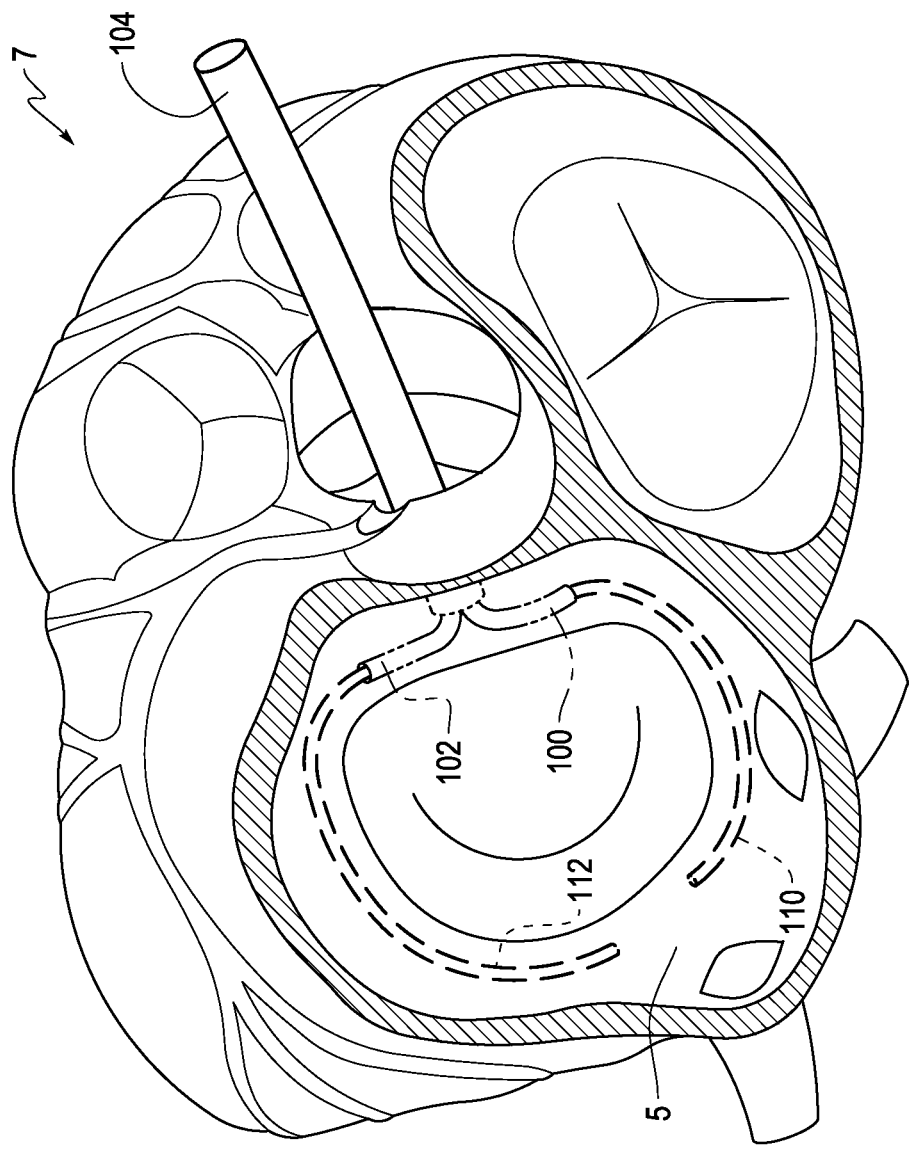

As can be seen from FIGS. 12A and 12B, a first delivery catheter 100 and a second delivery catheter 102, which are separate from each other (separate catheters) and, hence, which do not create a single interior but separate interiors, are forwarded to the ventricular chamber 5 (here the left ventricular chamber) of the heart 7 for example via the aorta (here) or for example via the superior or inferior vena cava (in case of right ventricular chamber). The first and second delivery catheters may be forwarded via a (same) primary delivery catheter 104 providing the primary access to the ventricular chamber 5 via the aorta or the vena cava.

Figure 12E:
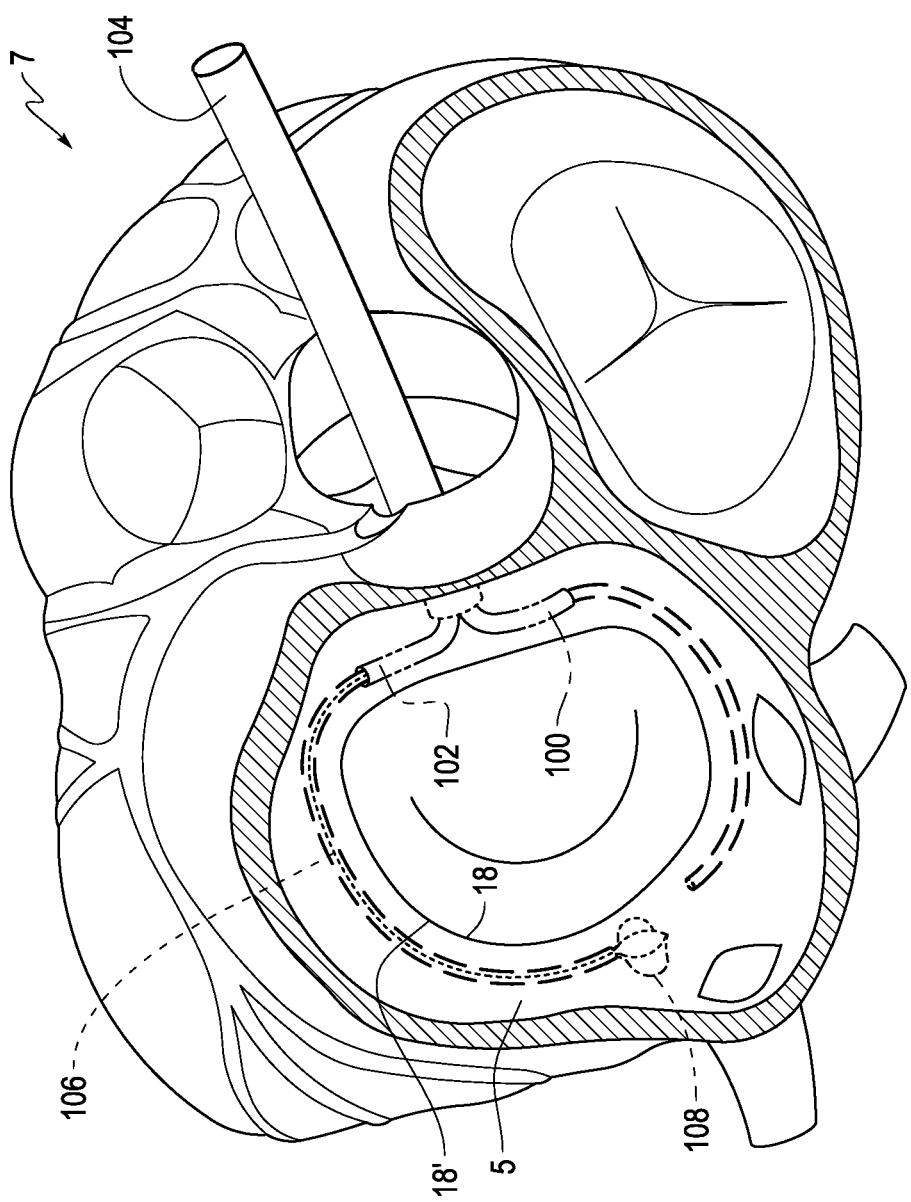
Figure 12F:
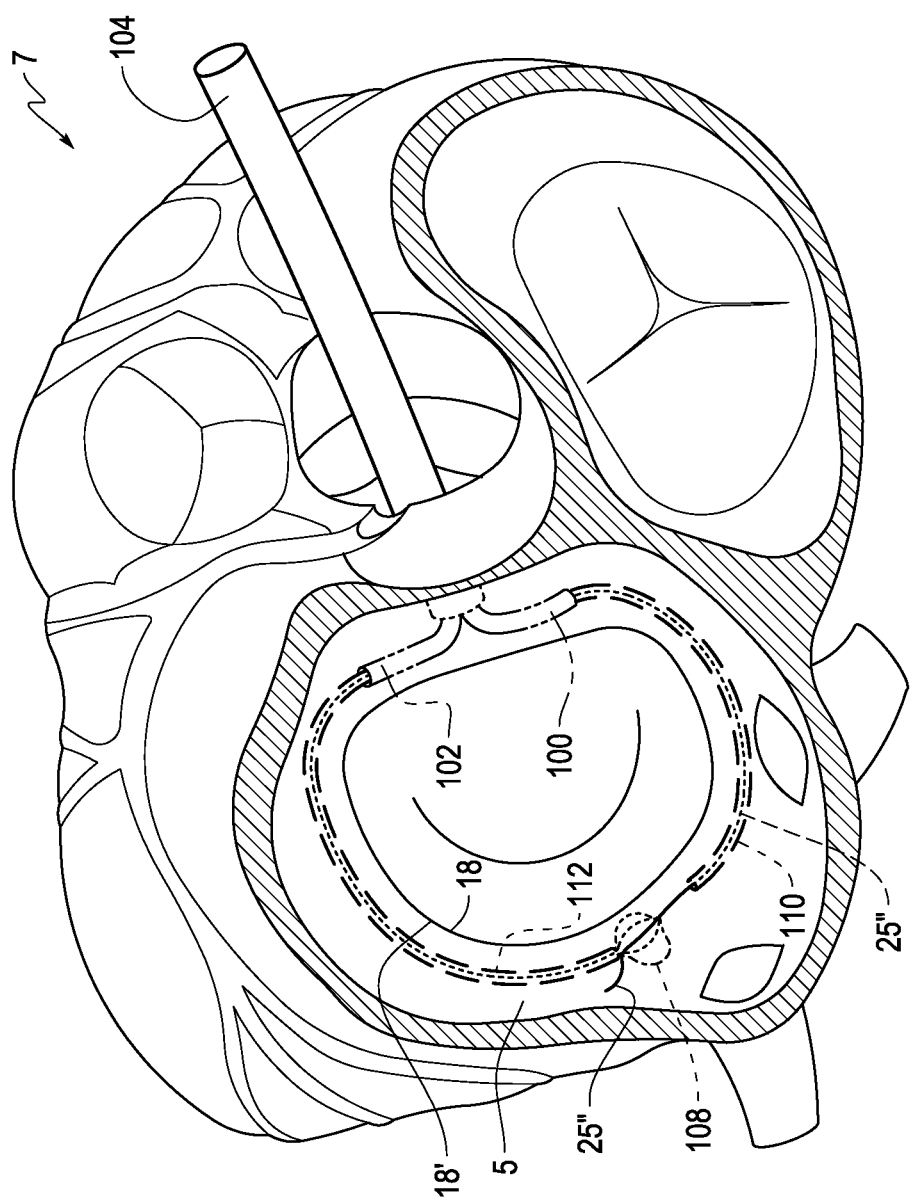
Figure 12G:
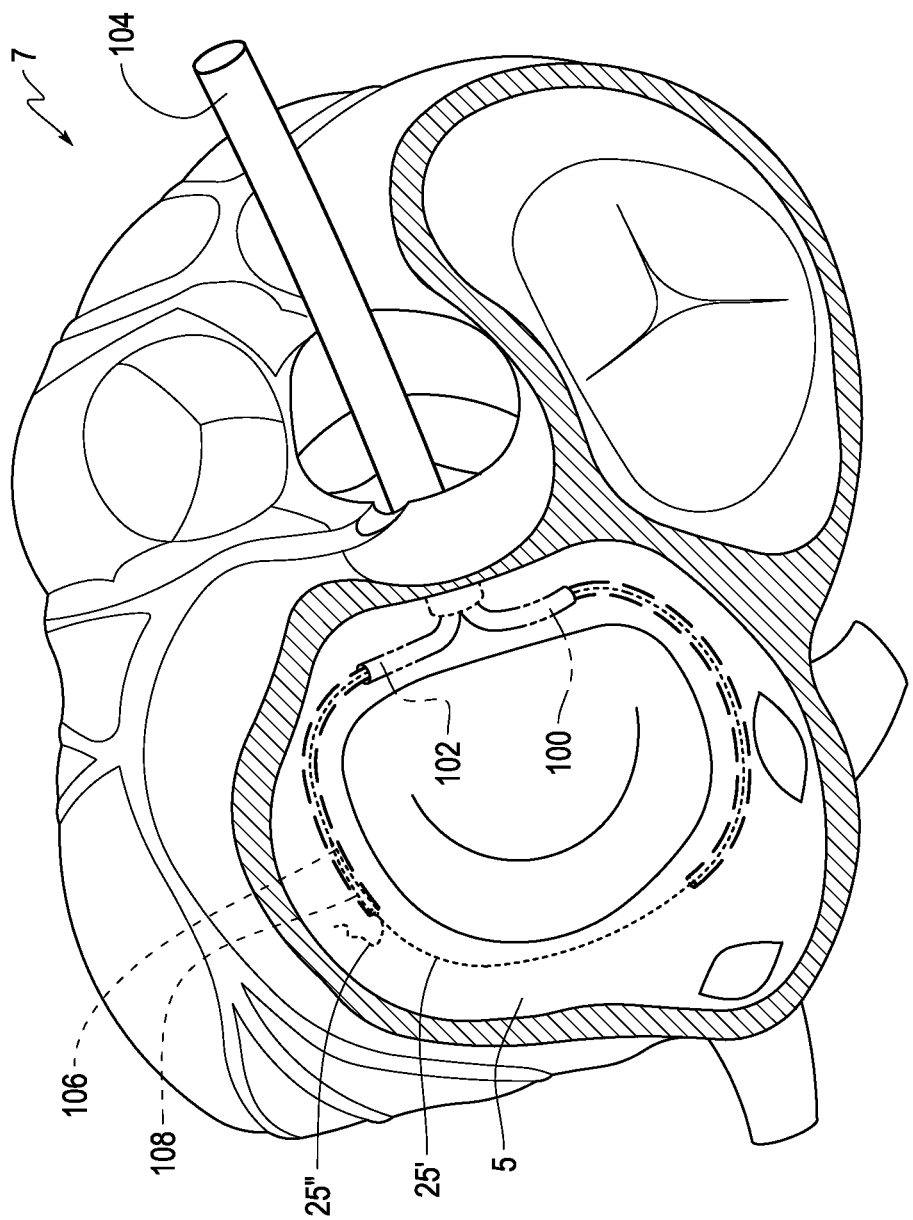
Figure 12H:
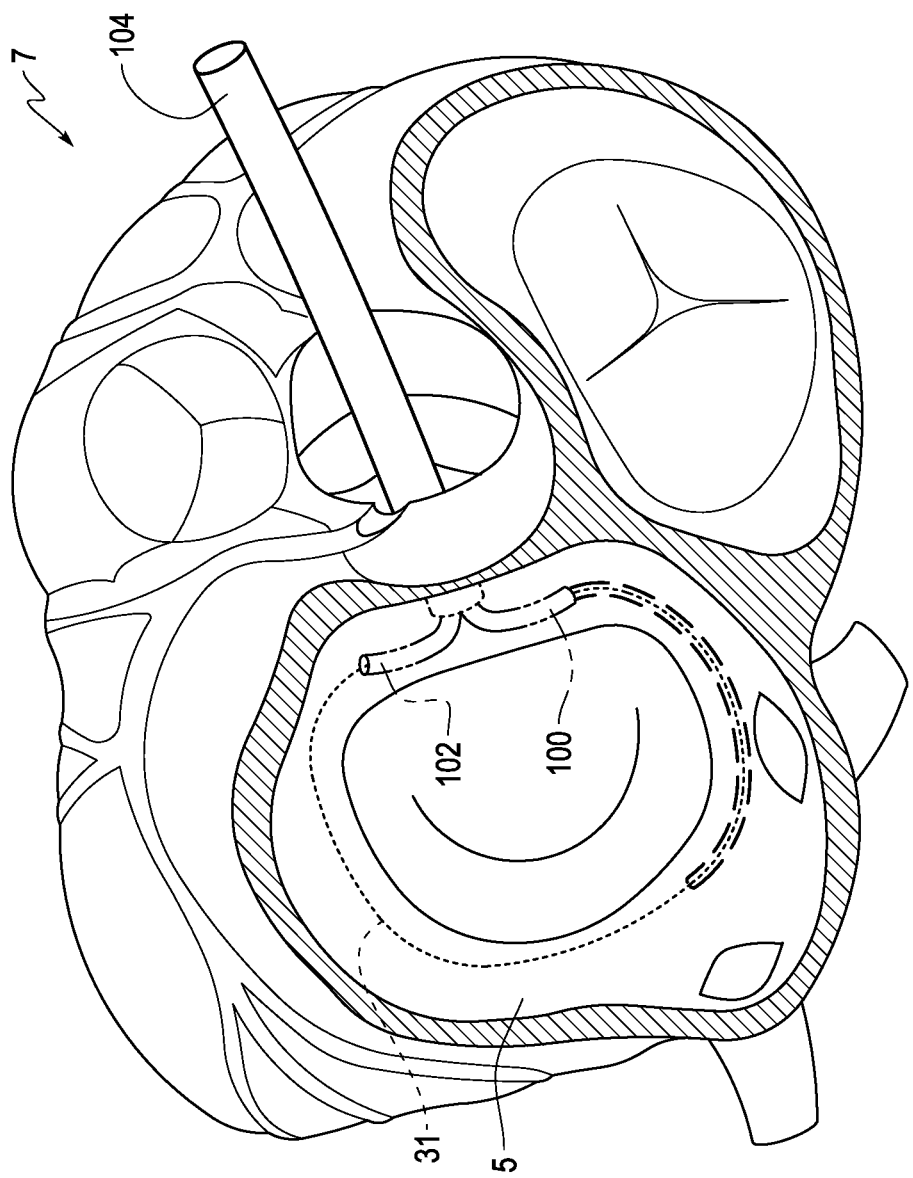
Figure 12I:
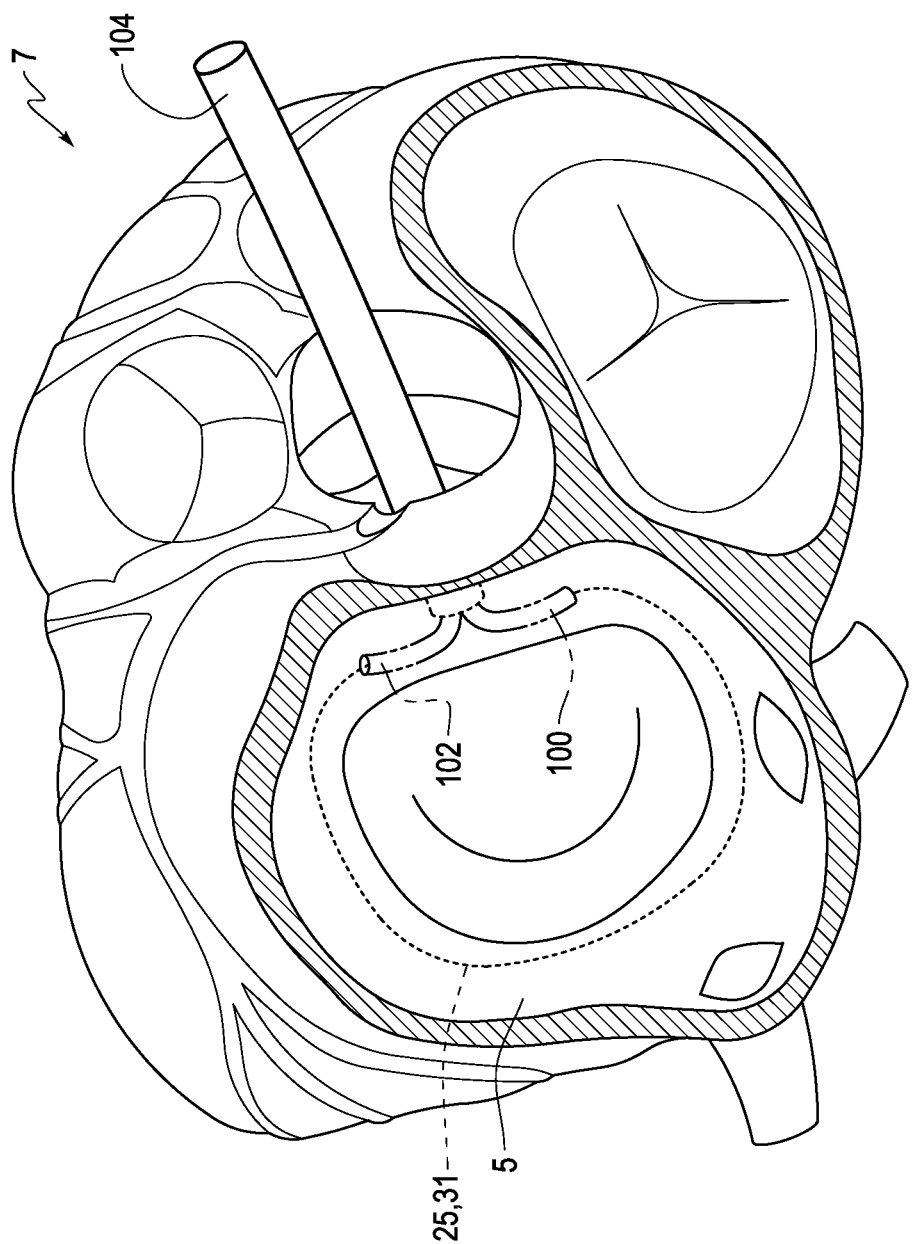
Figure 12J:
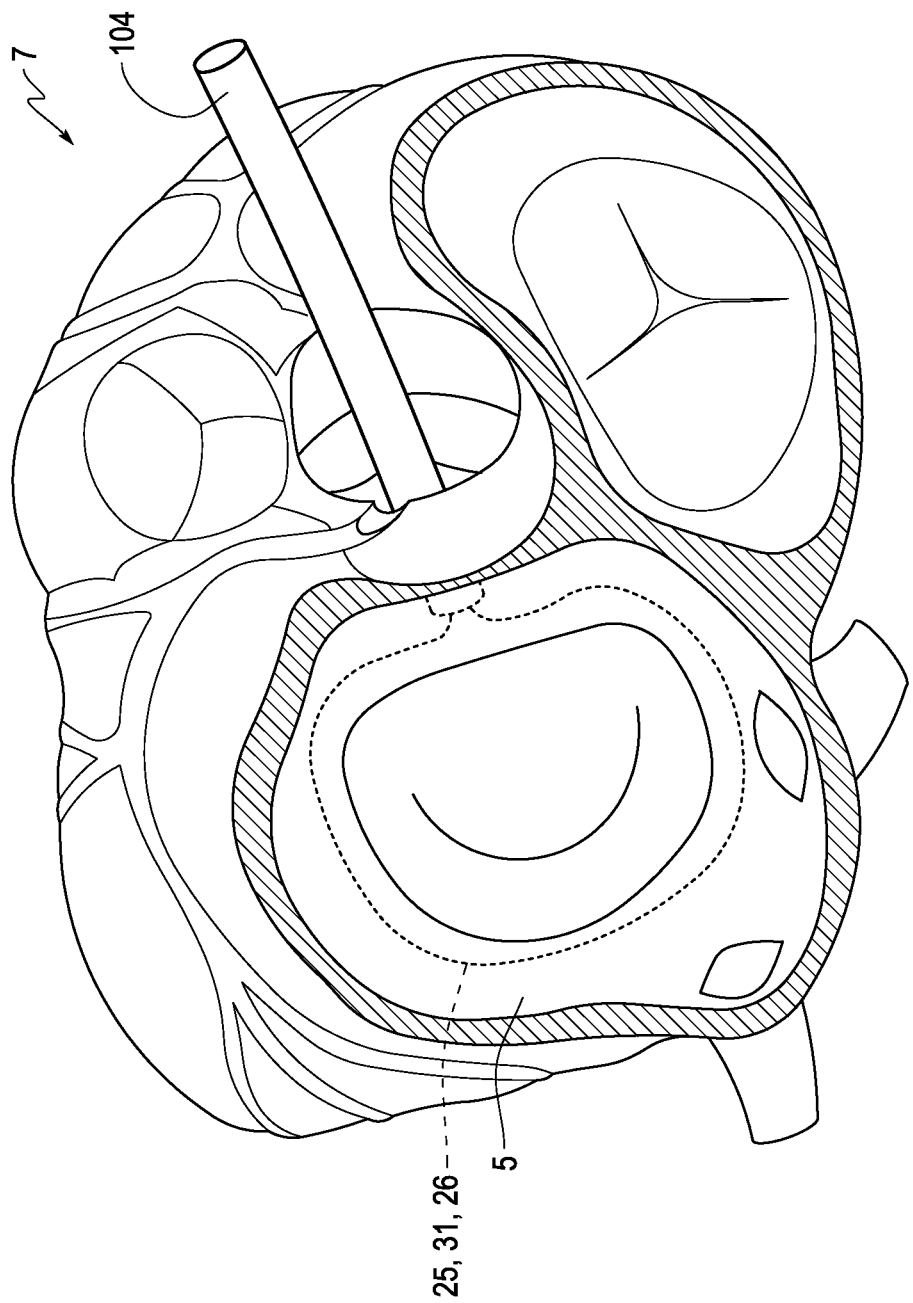

As can be seen from FIG. 12F and FIG. 12E a wire 25" is guided around about a circumferential portion, for example about the half circumference, of the circumferential connection channel wall structure 18' of the connection channel 18 via the first delivery catheter 100 in one circumferential direction of the circumferential connection channel wall structure 18', and a catching snare wire 106 with a catching basket 108 at a front end thereof (alternatively, for example, a catching snare 28 as shown in FIGS. 2A and 2B may be used instead of the catching basket 108) is guided around about the remaining circumferential portion, for example about the other half circumference, of the circumferential connection channel wall structure 18' of the connection channel 18 via the second delivery catheter 102 in the other circumferential direction of the circumferential connection channel wall structure 18', wherein the free end 25" will be guided through the three dimensional structure of the catching basket 108 (or through the two-dimensional opening of the catching snare 28) so as to be able to be caught by the catching basket 108 (or the catching snare 28).

The wire 25" and/or the catching wire 106 may be guided around the circumferential connection channel wall structure 18' by means of first and second auxiliary delivery catheters 110, 112, respectively, which auxiliary delivery catheters 110, 112 may have been previously forwarded through the first and second delivery catheters 100, 102 and may be of a shape-memory material provided to return the first and second auxiliary delivery catheters 110, 112 to assume a bow shape to be correspondingly able to automatically surround the circumferential connection channel wall structure 18' when being exposed from the first and second delivery catheters 100, 112. Accordingly, as can be seen from FIGS. 12C and 12D, the first and second auxiliary catheters 110 and 112 may be forwarded around the circumferential connection channel wall structure 18' before forwarding the wire 25' and the catching wire 106 therethrough.

As can be seen from FIG. 12G-12J, with the free end 25" of the wire 25' reliably caught in the catching basket 108 (or catching snare 28), the catching wire 106 is retracted back through the second delivery catheter 102 thereby guiding the wire 25' further around, for example completely around, the circumferential connection channel wall structure 18' to thereby form the loop 31 (also cf. FIG. 2C) to be further contracted to finally form the ring shaped outer device 25 or the device comprising the ring 26. The first and second auxiliary catheters 106, 108 may be retracted through the first and second delivery catheters 100, 102 (cf. FIGS. 12G and 12H) and then the first and second delivery catheters 100, 102 may be retracted (cf. FIG. 12I) through the primary delivery catheter 104 which itself may be retracted at latest. The inner device may be installed within the connection channel 18 in a manner as described above.

Figure 13A:
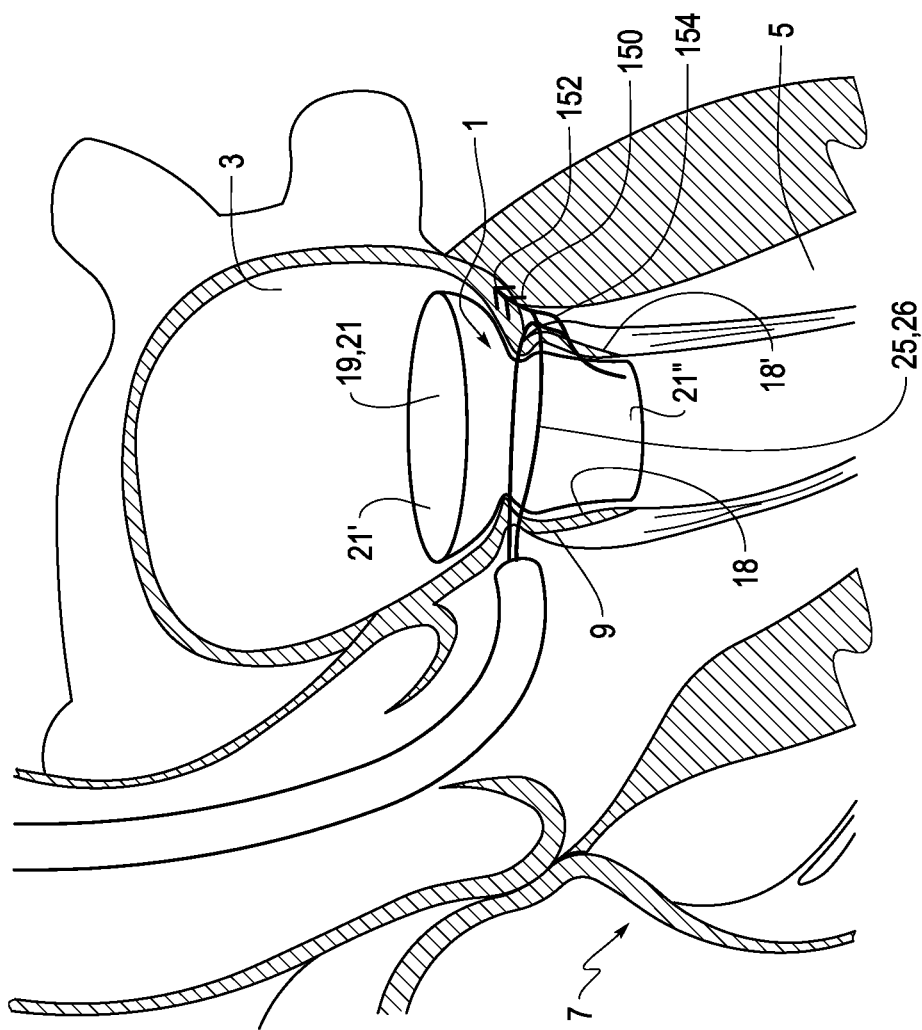
FIGS. 13A and 13B show a sectional perspective side view and a sectional perspective top view of a transcatheter atrio-ventricular valve prosthesis according to another embodiment of the invention.
Figure 13B:
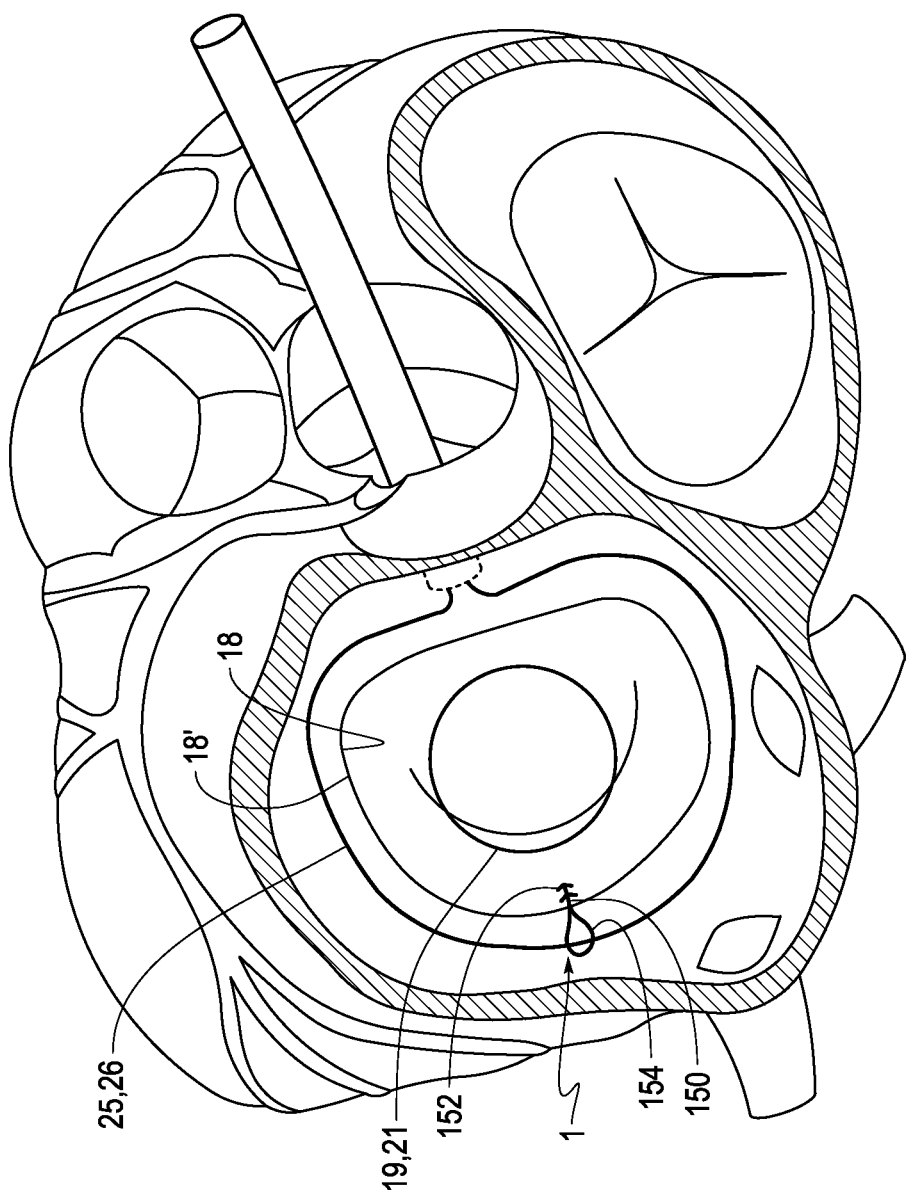

FIGS. 13A and 13B schematically show a perspective sectional side view and a perspective sectional top view of a transcatheter atrio-ventricular valve prosthesis 1 for functional replacement of an atrio-ventricular valve 9 in a connection channel 18, having a circumferential connection channel wall structure 18', between the atrial chamber 3 and the ventricular chamber 5 of a heart 7. The prosthesis comprises an inner device 19 (which may have a structure in a manner as the inner devices as explained above) to be disposed in the interior of the connection channel 18, the inner device 19 having a circumferential support structure 21 (which may have a structure in a manner as the circumferential support structures as explained above) which is radially expandable, and having a valve (which may have a structure in a manner as the valves as explained above) attached to the circumferential support structure 21. The circumferential support structure 21 of the inner device 19 is of tubular shape and extends along an axis and has two axial ends 21', 21", and an outer device 25 (which may generally have a structure in a manner as the outer devices as explained above) to be disposed on the exterior of the connection channel 18 (that is, of the circumferential connection channel wall structure 18'). The outer device 25 at least partly extends around the inner device 19 in a radial distance to the inner device 19, and whereby the inner and outer devices 21, 25 form a clamping mechanism for clamping the circumferential connection channel wall structure 18' therebetween. The outer device 25 comprises a ring 26, for extending circumferentially around the circumferential connection channel wall structure 18', arranged between and in a distance to the axial ends 21', 21" of the inner device 19. The outer device 25 further comprises an anchor member 150 having one or more anchor parts 152, such as barbs or hooks, to penetrate into the circumferential connection channel wall structure 18' at a position close to the ring 26. The anchor member 150 comprises an eye 154, through which the ring 26 extends to thereby be anchored on the circumferential connection channel wall structure 18' at this position by the anchor member 150. The eye 154 may have a three-dimensional catching basket structure as for example shown for the catching basket 108 in FIG. 12E.

Figure 14A:
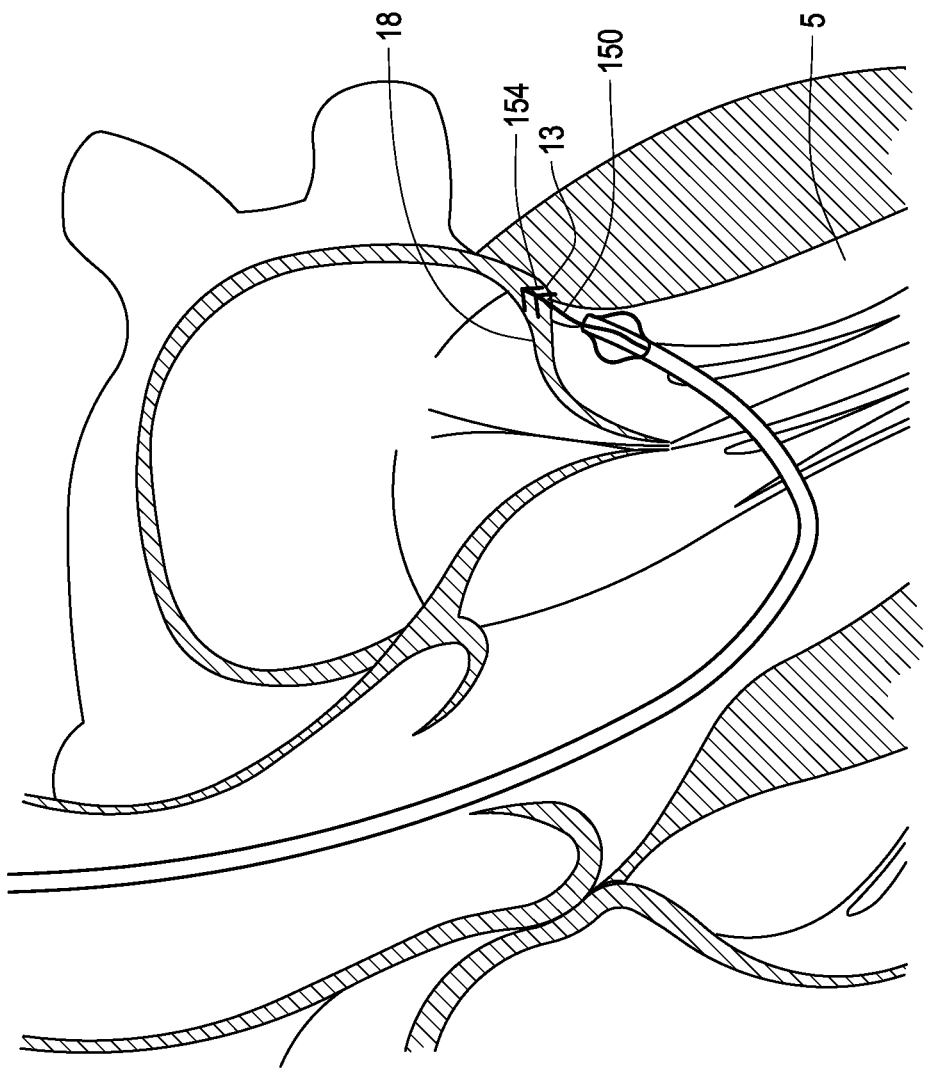
FIGS. 14A and 14B show sectional views for explaining an approach for implanting the prosthesis according to the embodiment of FIGS. 13A and 13B.
Figure 14B:
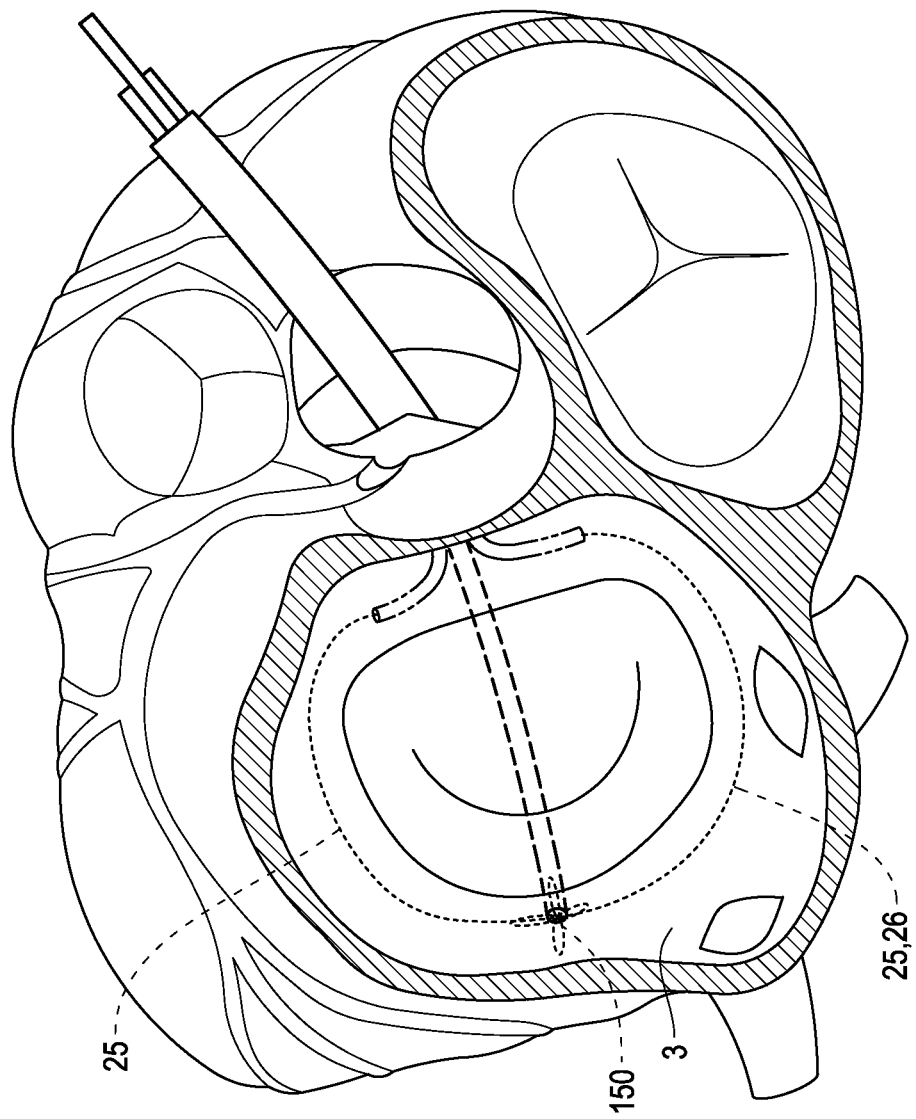

FIGS. 14A and 14B schematically show a sectional side view and a sectional top view, respectively, illustrating an approach for implanting the transcatheter atrio-ventricular valve prosthesis 1 according to the embodiment of FIGS. 13A and 13B. As can be seen from FIG. 14A, regarding implantation of the outer device 25, as a first step, the anchor member 150 may be delivered to the ventricular chamber 5 and penetrates with its anchor part or parts 154 into the circumferential connection channel wall structure 18', for example at a position at or adjacent to the annulus native valve annulus 13. With the anchor member 150 anchored in this position, the wire 25' may be guided around the circumferential connection channel wall structure 18' in a manner as described above to form the ring 26 of the outer device 25, wherein the wire 25' is guided through the eye 154 of the anchor member 150, whereby the wire 25' and the finalized ring 25 and thereby the outer device 126 are reliably positioned and fixed/anchored to the circumferential connection channel wall structure 18'. The inner device (not shown in FIGS. 14 and 14B) may be structured in any shape as described above and may be implanted according to any approach as explained above. On the basis of the structure of this embodiment, as an alternative aspect to clamping the circumferential connection channel wall structure 18' between the inner device 19 and the outer device 25, the inner device 25 may be fixed to the inner side of the circumferential connection channel wall structure 18' only by means of one or more anchor elements attached on the circumferential support structure and fixed to the circumferential connection channel wall structure 18' for example via penetrating the circumferential connection channel wall structure 18' and/or clamping, for example in manner as achieved by the staples 41, 43 as described above (cf. for example FIG. 6), the clips 51, 53, 55 as described above (cf. for example FIG. 7), the collar 65 as described above (cf. for example FIG. 8), the anchor elements 71 as described above (cf. for example FIG. 9) and/or other suitable anchors and for example in combination with the funnel portion 24 as described above (cf. for example FIG. 3). The outer device 25, for example the ring 26, may then not provide for a sufficient clamping action to secure inner device 19 within the connection channel 18, but may only provide for such a clamping force (in connection with the counter-force provided from the inner device 19) that a sealing effect/function is achieved between the circumferential connection channel wall structure 18' and the inner device 19 (the circumferential support structure 21 thereof).

Figure 15:
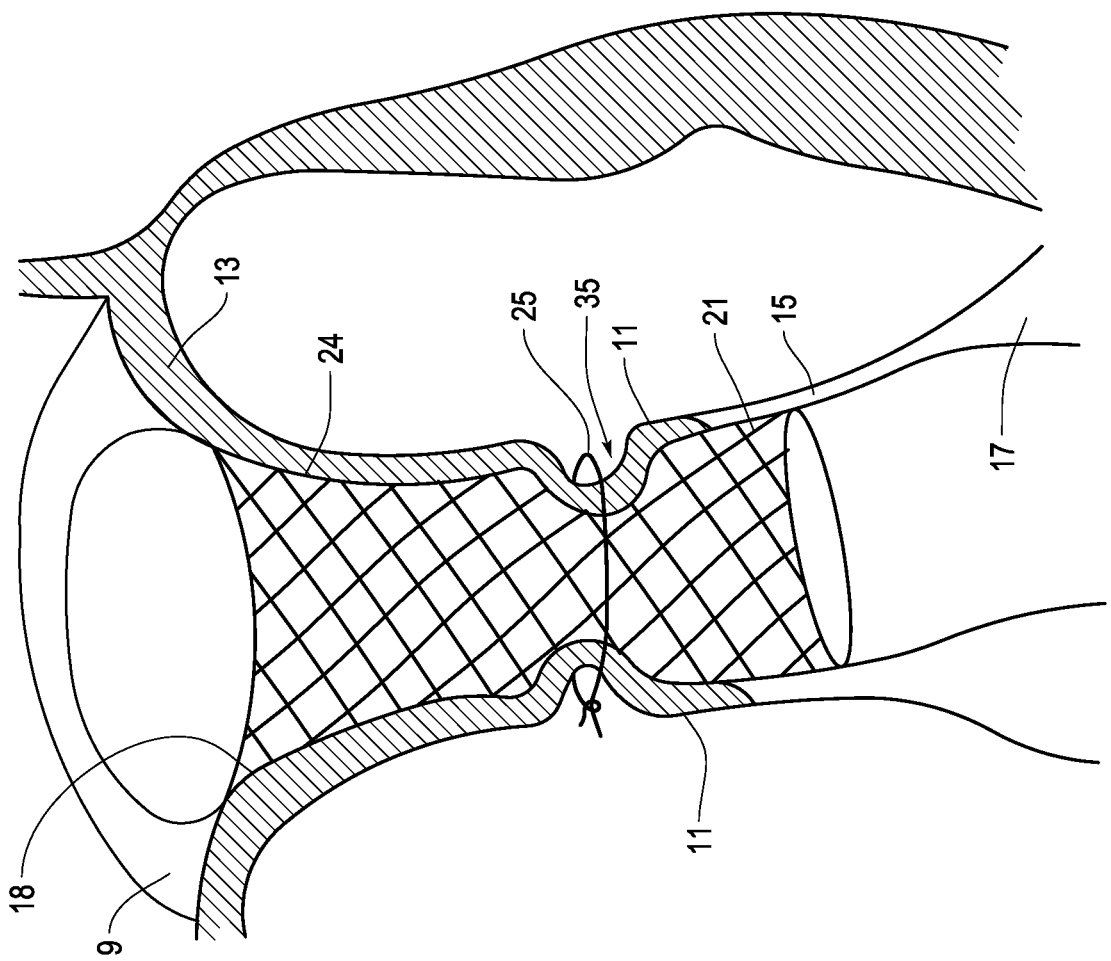
FIG. 15 shows a schematic perspective view of a transcatheter atrio-ventricular valve prosthesis according to another embodiment of the invention.
Figure 16:
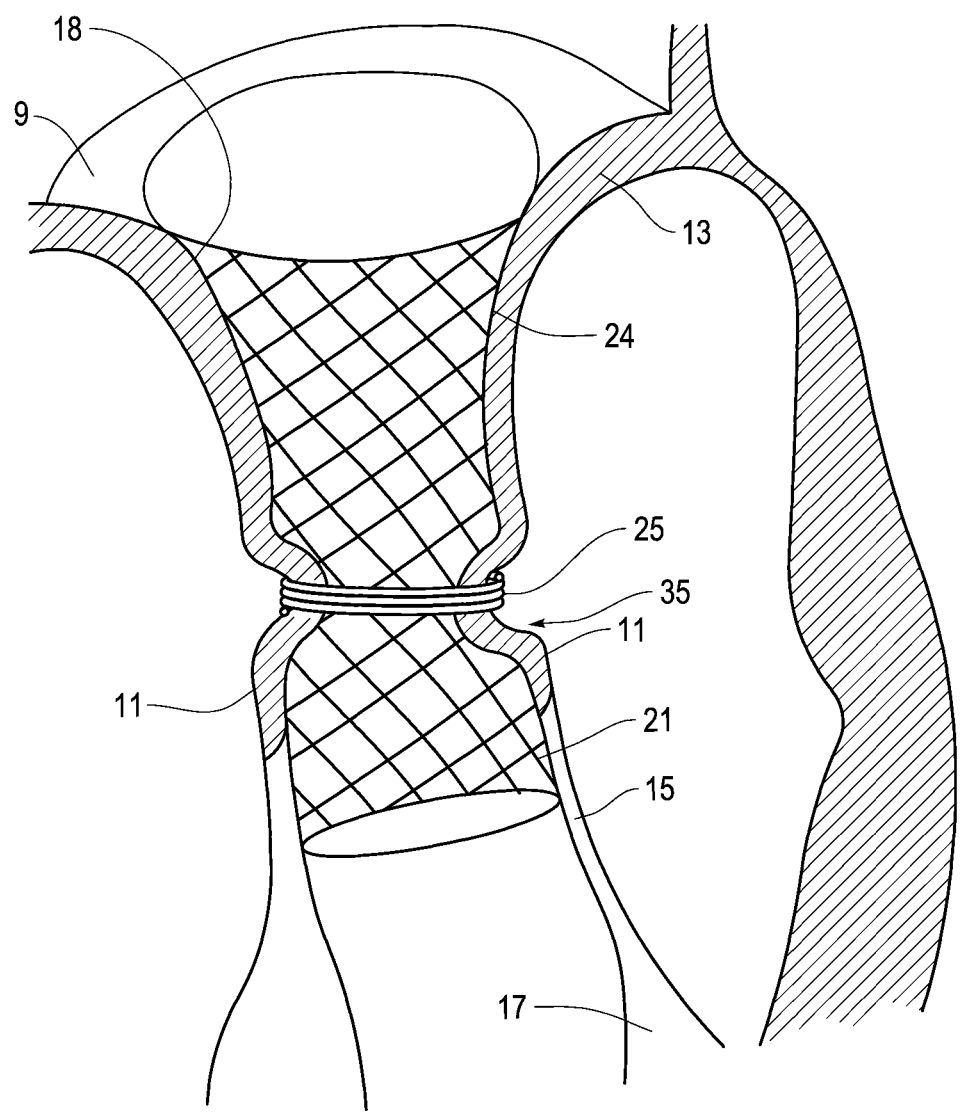
FIG. 16 shows a schematic perspective view of a transcatheter atrio-ventricular valve prosthesis according to an exemplary embodiment.

FIG. 15 shows a sectional side view in which the outer device 25 is employed to position the outer device 25 within the circumferential groove 35 to ensure proper positioning of the atrio-ventricular valve prosthesis 1 without frictionally securing the atrio-ventricular valve prosthesis 1 in place.

Various figures herein illustrate that the ring 26 of the outer device 25 remains positioned around the inner device 19 upon completion of the implantation of the atrio-ventricular (here mitral) valve prosthesis 1. However, the ring 26 of the outer device 25 can in embodiments be removed upon completion of the implantation. In such a case, the ring 26 of the outer device 25 may be used only during the implantation procedure to position the native valve leaflets 11 in a selected area to activate an anchoring mechanism, for example, as described herein, and may be subsequently removed. As illustrated in FIG. 15, the outer device 25 may be removed, for example, by opening the catching basket 108 in such a manner that the outer device 25 is released and can be removed through the second delivery catheter 100. Alternatively, the outer device 25 can be cut by a separate cutting mechanism, e.g., a catheter advanced over the outer device in place of the second delivery catheter 100. The outer device could also be cut by an electric current that leads to the heating and rupture of a selected weak point of the outer device. It could also be made of a resorbable material and be degraded over a certain period of time.

Although the invention has been described on the basis of embodiments, the invention is not intended to be restricted to these embodiments, but is intended to cover all modifications, equivalents and variations within the spirit and scope of the invention as disclosed herein. In this regard, for example, the described methods may be carried out on the beating heart or on the arrested heart.

The invention claimed is:

1. A transcatheter atrio-ventricular valve prosthesis disposable in a connection channel of a native heart valve between atrial and ventricular chambers of a heart having a circumferential connection channel wall structure, the transcatheter atrio-ventricular valve prosthesis comprising:
    an inner device including an inflow end and an outflow end and comprising a support structure that is radially expandable, the support structure including on an outer periphery thereof a compressible structure that is configured to be compressed into a compressed state when the prosthesis is deployed in the connection channel of the native heart valve;
    a valve disposed within and attached to the inner device; and
    an outer device comprising a plurality of arms coupled to an outflow end of the inner device, the plurality of arms extending from the outflow end towards the inflow end of the inner device, each arm of the plurality of arms having a single axial end that is connected to the support structure and a free end, the plurality of arms being configured to:
        receive a portion of the circumferential connection channel wall structure, and clamp the portion of the circumferential connection channel wall structure in a groove formed between the plurality of arms and the inner device by compressing the compressible structure into a compressed state when the prosthesis is deployed in the connection channel of the native heart valve, and
        radially wrap free ends of native valve leaflets of the connection channel wall structure.

2. The prosthesis according to claim 1, wherein the support structure includes a tubular funnel portion in which a portion of the support structure is tapered along an axial direction.

3. The prosthesis according to claim 2, wherein the tubular funnel portion is spaced proximally in the axial direction from the groove.

4. The prosthesis according to claim 2, wherein a taper of the tubular funnel portion is present at a terminal inflow end of the support structure.

5. The prosthesis according to claim 2, wherein the tubular funnel portion is configured to be implanted in the native valve so as to not cover an atrial side of an annulus of the native heart valve.

6. The prosthesis according to claim 2, wherein the tubular funnel portion is configured to be implanted in between the native valve leaflets in an area of an annulus of the native heart valve.

7. The prosthesis according to claim 1, wherein the inner device includes a tubular stent.

8. The prosthesis according to claim 7, wherein the stent is a self-expanding stent.

9. The prosthesis according to claim 1, wherein the groove includes a radial gap formed between the inner device and the plurality of arms when the compressible structure is compressed into the compressed state.

10. The prosthesis according to claim 1, wherein the plurality of arms is fixedly connected to and distributed around an outer periphery of the inner device to form a collar there around.

11. The prosthesis according to claim 1, wherein the support structure is radially expandable to be able to exert an active outward radial force against an inner periphery of the circumferential connection channel wall structure.

12. The prosthesis according to claim 1, wherein the support structure is made of a mesh-like structure.

13. The prosthesis according to claim 1, wherein the outer device further comprises a ring structure wound circumferentially around the inner device to form one or more rings there around.

14. The prosthesis according to claim 13, wherein the ring structure is configured to circumferentially clamp the connection channel wall structure radially between the ring structure and the inner device.

15. The prosthesis according to claim 13, wherein the ring structure is wound circumferentially around the inner device at a position between the inflow end and the outflow end of the inner device.

16. The prosthesis according to claim 13, wherein the ring structure is contractible to be able to exert an active inward radial force against an outer periphery of the circumferential connection channel wall structure.

17. The prosthesis according to claim 1, wherein all of the arms comprised by the prosthesis extend in a direction from the outflow end of the support structure towards the inflow end of the support structure.

18. The prosthesis according to claim 1, wherein the groove is configured to contact an inner periphery of the connection channel wall structure.

19. The prosthesis according to claim 1, wherein the plurality of arms are configured to extend parallel to the inner device when the compressible structure is in the compressed state.

* * * * *